United States Patent
Kosuge et al.

(10) Patent No.: US 8,829,502 B2
(45) Date of Patent: Sep. 9, 2014

(54) CONDENSED POLYCYCLIC COMPOUND AND ORGANIC LIGHT EMITTING ELEMENT INCLUDING THE SAME

(75) Inventors: Tetsuya Kosuge, Yokohama (JP); Jun Kamatani, Tokyo (JP); Kenichi Ikari, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 146 days.

(21) Appl. No.: 13/590,973

(22) Filed: Aug. 21, 2012

(65) Prior Publication Data
US 2013/0048965 A1    Feb. 28, 2013

(30) Foreign Application Priority Data
Aug. 23, 2011 (JP) .................. 2011-181580

(51) Int. Cl.
*H01L 35/24* (2006.01)

(52) U.S. Cl.
USPC ................................. 257/40; 257/E51.001

(58) Field of Classification Search
USPC ............................................ 257/40, E51.001
See application file for complete search history.

(56) References Cited

U.S. PATENT DOCUMENTS

2010/0176716 A1    7/2010 Igawa et al.

FOREIGN PATENT DOCUMENTS

| CN | 1874979 A | 12/2006 |
|---|---|---|
| JP | 11-026158 A | 1/1999 |
| WO | 2008/120806 A1 | 10/2008 |

*Primary Examiner* — Anthony Ho
(74) *Attorney, Agent, or Firm* — Canon U.S.A., Inc., IP Division

(57) ABSTRACT

A condensed polycyclic compound which emits green light and which has a high chemical stability and an organic light emitting element including the same are provided. A condensed polycyclic compound represented by the general formula [1] or [2] described in claim 1 is provided. In the formula [1] and [2], $R_1$ to $R_{10}$ are independently selected from the group consisting of a hydrogen atom, a straight or branched alkyl group having 1 to 4 carbon atoms, and a substituted or unsubstituted aromatic hydrocarbon group having 6 to 22 carbon atoms.

12 Claims, 2 Drawing Sheets

CONDENSED POLYCYCLIC COMPOUND AND ORGANIC LIGHT EMITTING ELEMENT INCLUDING THE SAME

BACKGROUND OF THE INVENTION

1. Field of the Invention

The present invention relates to a novel condensed polycyclic compound and an organic light emitting element including the same.

2. Description of the Related Art

An organic light emitting element is an element which has an anode, a cathode, and an organic compound layer arranged between these two electrodes. In the organic light emitting element, an exciton is generated when a hole and an electron, which are injected from the respective electrodes, are recombined with each other in the organic compound layer, and light is emitted when the exciton returns to the ground state.

The recent advances in the organic light emitting element are remarkable, and a high-speed response, thin, and lightweight light emitting device which can be driven at a low voltage and which has various light emitting wavelengths can be formed.

When the organic light emitting element is applied to a full color display and the like, light emitting materials for the respective colors, blue, green, and red, are each required to be highly purified, and the light emitting efficiency and durability life of the light emitting element have also been requested to be further improved.

As a light emitting material used for a light emitting layer of the organic light emitting element, for example, the following compounds A and B have been disclosed in Japanese Patent Laid-Open No. 11-026158 (no corresponding foreign application) as a compound having a fluorantheno[8,9-b]triphenylene ring as a main skeleton.

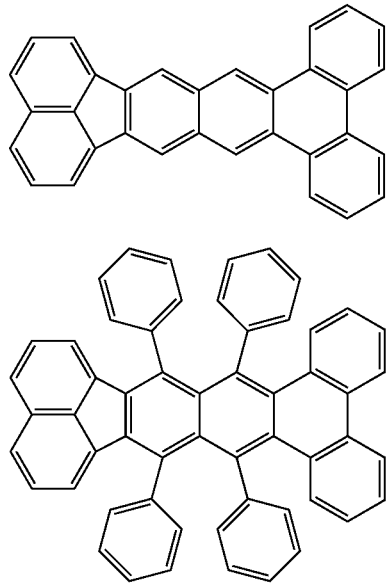

A

B

Emission colors of the compounds A and B disclosed in Japanese Patent Laid-Open No. 11-026158 (no corresponding foreign application) are both blue, and green light emission is difficult to obtain by a compound having a fluorantheno[8,9-b]triphenylene ring as a main skeleton.

Although the light emitting wavelength can be increased when a substituent is provided on the main skeleton of the compound, the chemical stability thereof may be degraded in some cases.

SUMMARY OF THE INVENTION

Aspects of the present invention provide a novel highly chemically stable condensed polycyclic compound which can emit green light without any substituents on the main skeleton. In addition, aspects of the present invention also provide an organic light emitting element which includes the above compound and which has a high light emitting efficiency and excellent drive durability.

Accordingly, aspects of the present invention provide a condensed polycyclic compound represented by the following general formula [1] or [2].

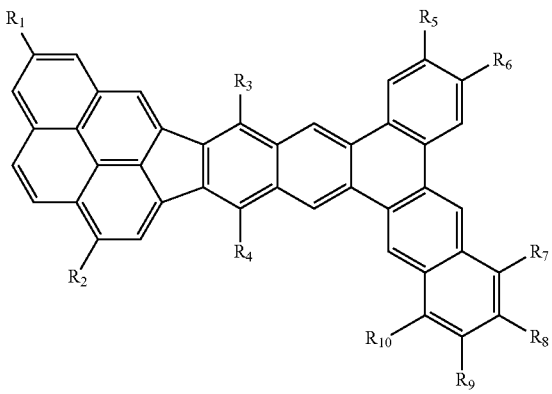

[1]

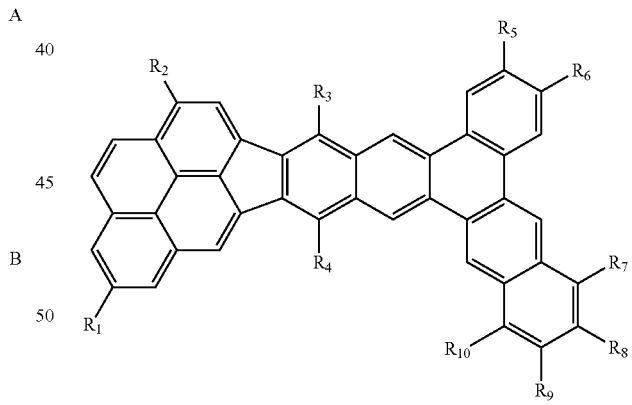

[2]

In the formulas [1] and [2], $R_1$ to $R_{10}$ are each independently selected from the group consisting of a hydrogen atom, a straight or branched alkyl group having 1 to 4 carbon atoms, and a substituted or unsubstituted aromatic hydrocarbon group having 6 to 22 carbon atoms.

According to aspects of the present invention, a novel highly chemically stable condensed polycyclic compound which can emit green light can be provided. In addition, aspects of the present invention also provide an organic light emitting element which includes the above compound and which has a high light emitting efficiency and excellent drive durability.

Further features of the present invention will become apparent from the following description of exemplary embodiments with reference to the attached drawings.

DESCRIPTION OF THE EMBODIMENTS

Figure 1:
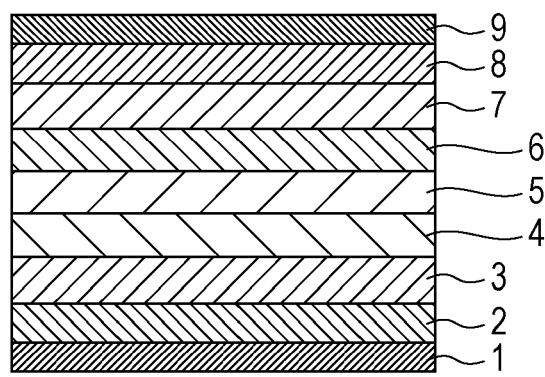
FIG. 1 is a schematic view showing one example of a laminated light emitting layer type organic light emitting element according to the embodiment.

Aspects of the present invention relate to a condensed polycyclic compound represented by the following general formula [1] or [2].

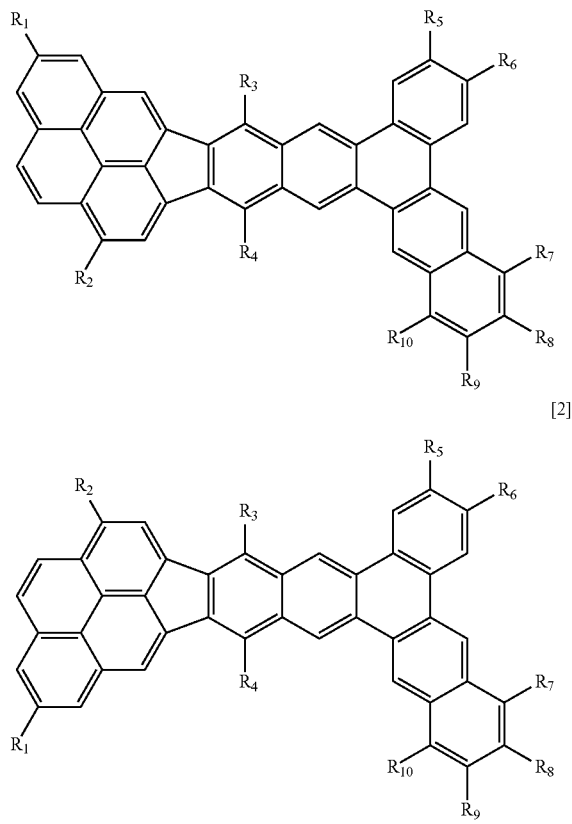

In the formulas [1] and [2], $R_1$ to $R_{10}$ are each independently selected from the group consisting of a hydrogen atom, a straight or branched alkyl group having 1 to 4 carbon atoms, and a substituted or unsubstituted aromatic hydrocarbon group having 6 to 22 carbon atoms.

As particular examples of the straight or branched alkyl group having 1 to 4 carbon atoms represented by $R_1$ to $R_{10}$, a methyl group, an ethyl group, an n-propyl group, an iso-propyl group, an n-butyl group, an iso-butyl group, a sec-butyl group, and a tert-butyl group may be mentioned.

As particular examples of the aromatic hydrocarbon group having 6 to 22 carbon atoms represented by $R_1$ to $R_{10}$, there may be mentioned a phenyl group, a biphenyl group, a ter- phenyl group, a naphthyl group, a fluorenyl group, a phenanthryl group, an anthracenyl group, a fluoranthenyl group, a pyrenyl group, a chrysenyl group, a benzo[a]anthracenyl group, a tetracenyl group, a benzo[c]phenanthryl group, a benzo[ghi]fluoranthenyl group, a perylenyl group, a benzo[e]pyrenyl group, a benzo[a]fluoranthenyl group, a benzo[b]fluoranthenyl group, a benzo[j]fluoranthenyl group, a benzo[k]fluoranthenyl group, a picenyl group, a benzo[b]triphenylenyl group, a benzo[b]chrysenyl group, an indeno[1,2,3-cd]fluoranthenyl group, and an indeno[1,2,3-cd]pyrenyl group.

In one case, among the above aromatic hydrocarbon groups, a phenyl group, a biphenyl group, a terphenyl group, a fluorenyl group, a phenanthryl group, a fluoranthenyl group, and a pyrenyl group may be provided.

The above aromatic hydrocarbon group having 6 to 22 carbon atoms may have a substituent. For example, there may be mentioned an alkyl group, such as a methyl group, an ethyl group, an n-propyl group, an iso-propyl group, an n-butyl group, an iso-butyl group, a sec-butyl group, a tert-butyl group, an n-hexyl group, a cyclohexyl group, or an adamantyl group; an aromatic hydrocarbon group, such as a phenyl group, a biphenyl group, a terphenyl group, a naphthyl group, a fluorenyl group, a phenanthryl group, an anthracenyl group, a pyrenyl group, a chrysenyl group, a triphenylenyl group, a fluoranthenyl group, a tetracenyl group, or a picenyl group; an aromatic heterocyclic group, such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl groups, a phenazinyl group, a phenoxazinyl group, a phenothiazinyl group, a benzothiophenyl group, a dibenzothiophenyl group, a benzofuranyl group, a dibenzofuranyl group, an oxazolyl group, or an oxadiazolyl group; a substituted amino group, such as a dimethylamino group, a diethylamino group, a dibenzylamino group, a diphenylamino group, a ditolylamino group, a dinaphthylamino group, or a difluorenylamino group; an alkoxy group, such as a methoxy group or an ethoxy group; an aryloxy group, such as a phenoxy group or a naphthoxy group; a halogen atom, such as fluorine, chlorine, bromine, or iodine; a vinyl group, an acrylate group, a methacrylate group, an oxetanyl group, a hydroxyl group, a cyano group, and a nitro group.

The condensed polycyclic compound represented by the formula [1] or [2] may be a compound represented by formula [3] or [4].

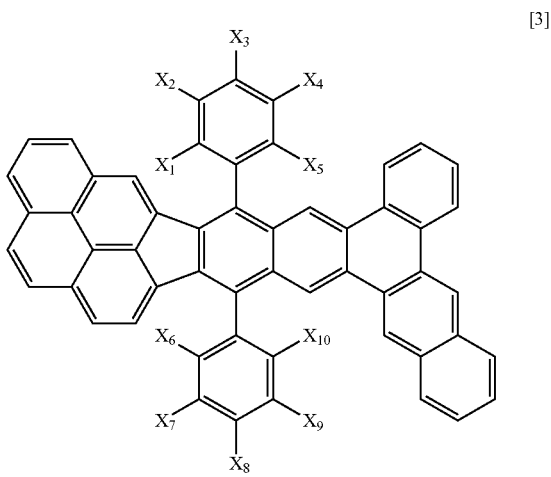

[4]

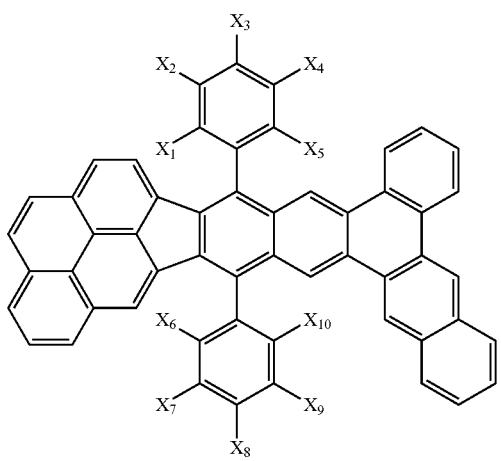

In the formulas [3] and [4], $X_1$ to $X_{10}$ are each independently selected from the group consisting of a hydrogen atom, a straight or branched alkyl group having 1 to 4 carbon atoms, and a substituted or unsubstituted phenyl group.

Particular examples of the straight or branched alkyl group having 1 to 4 carbon atoms represented by $X_1$ to $X_{10}$ are similar to the particular examples of the straight or branched alkyl group having 1 to 4 carbon atoms represented by $R_1$ to $R_{10}$ in the formulas [1] and [2].

The above phenyl group may have a substituent. Particular examples of the substituent which this phenyl group may further have are similar to the particular examples described as the substituent which the aromatic hydrocarbon group having 6 to 22 carbon atoms represented by $R_1$ to $R_{10}$ in the formulas [1] and [2] may further have.

(Properties of Condensed Polycyclic Compound According to Aspects of the Present Invention)

The condensed polycyclic compound according to aspects of the present invention has benzo[6',7']triphenyleno[2',3':5, 6]indeno[1,2,3-cd]pyrene (hereinafter simply referred to as "BTIPy(a)") or benzo[10',11']triphenyleno[2',3':5,6]indeno [1,2,3-cd]pyrene (hereinafter simply referred to as "BTIPy (b)") as a main skeleton.

BTIPy(a)

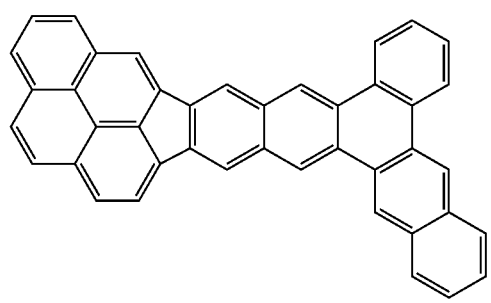

Benzo[6', 7']triphenyleno[2', 3':5, 6] indeno[1,2,3-cd]pyrene

BTIPy(b)

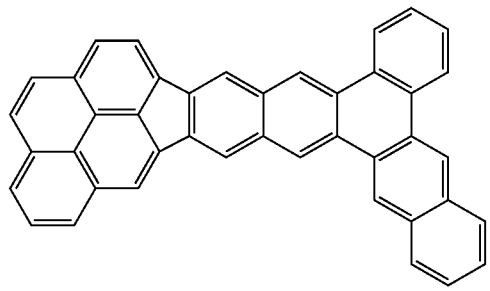

Benzo[10', 11']triphenyleno[2', 3':5, 6] indeno[1,2,3-cd]pyrene

The above two condensed polycyclic compounds are in a diastereomeric relationship, and because of a synthetic method which will be described layer, it is difficult to isolate one derivative of the above two compounds by a selective synthetic method and/or refining.

Hence, the condensed polycyclic compound according to aspects of the present invention may be a mixture of the two diastereomers represented by the general formulas [1] and [2].

Since the diastereomers have almost the equivalent physical properties to each other, even if the mixture thereof is used, troubles in terms of material physical properties hardly occur. Hereinafter, the two diastereomers are collectively called BTIPy.

The condensed polycyclic compound according to aspects of the present invention is represented by the general formula [1] or [2] and has the above BTIPy ring as a main skeleton.

In this embodiment, the main skeleton of the compound indicates a partial structure having the largest π conjugated structure in the compound molecule, and this partial structure primarily determines the physical properties of the whole compound, such as the S1 energy, the T1 energy, the HOMO level, the LUMO level, the oscillator strength, and the light emitting quantum yield.

On the other hand, an accessory skeleton is an auxiliary partial structure in the compound molecule and has not a significant influence to the physical properties of the whole compound which are determined by the above main skeleton but is used for fine adjustment.

In particular, in the condensed polycyclic compounds represented by the general formulas [1] and [2] according to aspects of the present invention, the substituents $R_1$ to $R_{10}$ each correspond to the accessory skeleton.

That is, regardless of the types of substituents $R_1$ to $R_{10}$, condensed polycyclic compounds each having the BTIPy ring represented by the formula [1] or [2] as the main skeleton are expected to have almost equivalent physical properties to each other.

The condensed polycyclic compound according to aspects of the present invention is a compound having BTIPy as the main skeleton.

BTIPy has the structure in which a naphthalene ring and a benzene ring are condensed to a fluoranthene side and a triphenylene side of fluorantheno[8,9-b]triphenylene, respectively, as shown below.

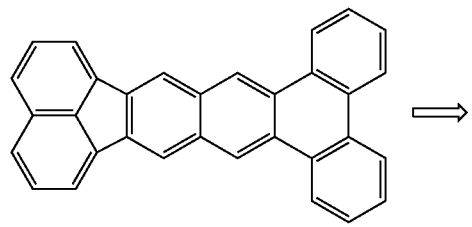

Fluorantheno[8,9-b]triphenylene

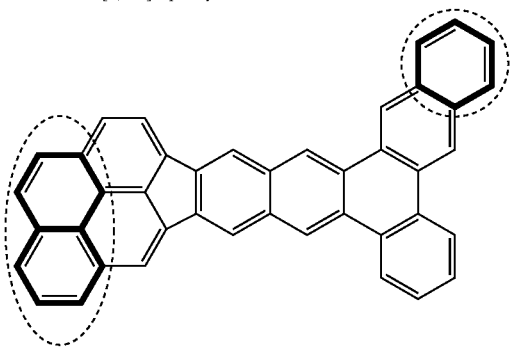

Benzo[6', 7']triphenyleno[2', 3':5, 6]
indeno[1,2,3-cd]pyrene

When a naphthalene ring and a benzene ring are condensed to fluorantheno[8,9-b]triphenylene which emits blue light to expand the π conjugated plane as described above, the S1 energy of the compound can be decreased, and the wavelength of light emission color can be increased. As a result, BTIPy exhibits green light emission.

The green light emission in this case is light emission in which the emission peak wavelength in a toluene diluted solution of a light emitting material is in a range of 475 to 510 nm.

When this light emitting material is used as a guest material of a light emitting layer of an organic light emitting element, the emission peak wavelength thereof is in a range of 500 to 540 nm, and green light emission having a high color purity can be obtained.

The reason for this is that between the toluene diluted solution and the light emitting element, a difference in emission peak wavelength of approximately 0.15 eV is generally generated.

In addition, condensed polycyclic rings each obtained by condensing at least one aromatic ring to the fluorantheno[8,9-b]triphenylene ring are present besides the BTIPy ring according to aspects of the present invention.

For typical condensed polycyclic rings among those compounds, molecular orbital calculation was performed, and the results thereof are shown in the following Table 1.

In general, in a compound which exhibits fluorescent emission, the S1 energy corresponds to the emission peak wavelength, and the fluorescence quantum yield is increased as the oscillator strength is increased.

TABLE 1

| Structural Formula | | S1 Energy (Equivalent Wavelength Value/nm) | Oscillator Strength |
|---|---|---|---|
| Fluorantheno[8,9-b]triphenylene | | 413 | 0.266 |
| Comparative Compound C1 | | 431 | 0.215 |

TABLE 1-continued
| Structural Formula | S1 Energy (Equivalent Wavelength Value/nm) | Oscillator Strength |
|---|---|---|
| Condensed Ring 1 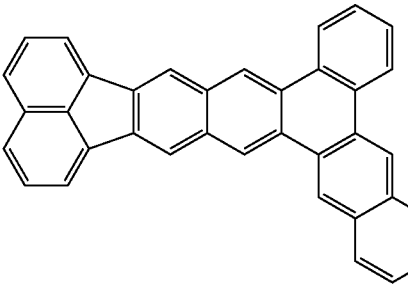 | 420 | 0.243 |
| Condensed Ring 2 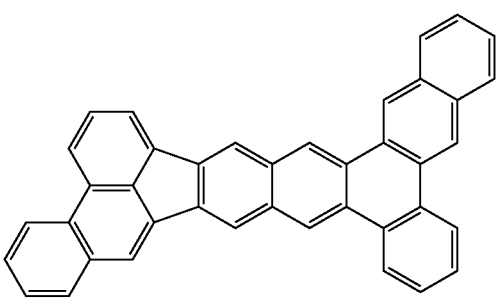 [SMILES: c1ccc2cc3c(cc2c1)c1ccccc1c1cc2cc4c(cc2cc13)-c1cccc2c1c-4cc1ccccc12] | 420 | 0.216 |
| BTIPy(a) 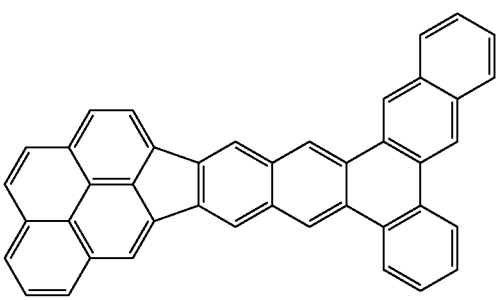 [SMILES: c1ccc2cc3c(cc2c1)c1ccccc1c1cc2cc4c(cc2cc13)-c1ccc2ccc3cccc5cc-4c1c2c35] | 451 | 0.434 |
| BTIPy(b) 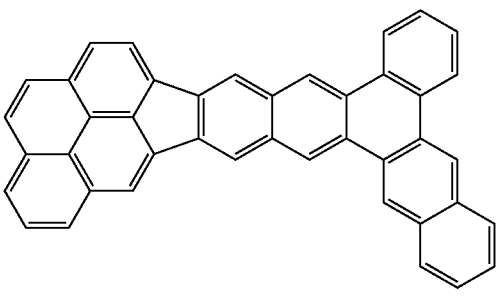 [SMILES: c1ccc2cc3c(cc2c1)c1ccccc1c1cc2cc4c(cc2cc13)-c1cc2cccc3ccc5ccc-4c1c5c32] | 451 | 0.424 |
| Example Compound 201(b) 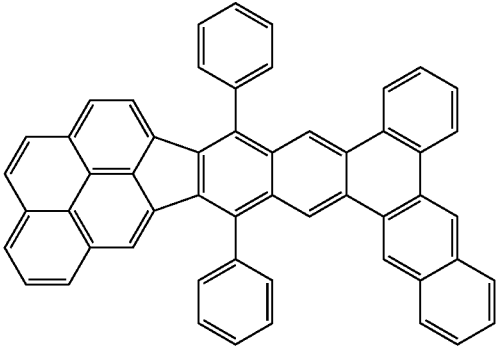 [SMILES: c1ccc(-c2c3c(c(-c4ccccc4)c4cc5c6cc7ccccc7cc6c6ccccc6c5cc24)-c2cc4cccc5ccc6ccc-3c2c6c54)cc1] | 452 | 0.441 |

TABLE 1-continued

| | Structural Formula | S1 Energy (Equivalent Wavelength Value/nm) | Oscillator Strength |
|---|---|---|---|
| Condensed Ring 3 | 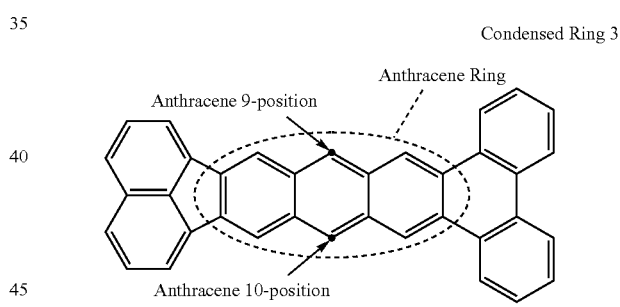 | 483 | 0.011 |

In a comparative compound C1 which is a fluorantheno[8,9-b]triphenylene derivative, although the calculated value of the S1 energy is 431 nm (2.88 eV), the actual measured value of the emission peak wavelength in a toluene diluted solution is 460 nm (2.70 eV).

Accordingly, since there is a difference of 0.18 eV between the calculated value and the actual measured value, when this difference is taken into consideration, in order to obtain the green light emission at an emission peak wavelength of 475 to 510 nm, the S1 energy obtained by calculation may be set in a range of 444 to 475 nm.

It is believed that when one or two benzene rings are simply increased by condensation to fluorantheno[8,9-b]triphenylene as in the cases of the condensed rings 1 and 2 in Table 1, the expansion of the π conjugation is not sufficient, and the green light emission is not obtained.

However, in the BTIPy ring according to aspects of the present invention, since the condensed rings corresponding to three benzene rings are increased, the calculated value of the S1 energy is set to 451 nm, so the condition of the above green light emission is satisfied.

The reason the light emission wavelength can be increased to realize the green light emission as described above is that the BTIPy ring includes a pyrene ring as a partial structure in the condensed ring as described below in which a wide π conjugated plane can be obtained.

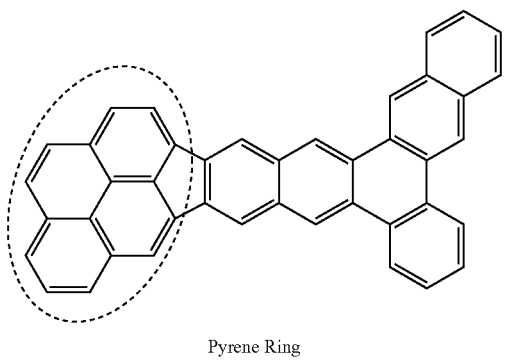

BTIPy(a)

Pyrene Ring

Hence, in the BTIPy ring according to aspects of the present invention, the wavelength can be effectively increased from that of fluorantheno[8,9-b]triphenylene when the necessary minimum number of the condensed ring is increased, so that the green light emission can be obtained.

If the condensed rings corresponding to four benzene rings or more are increased, although the wavelength can be easily increased, in one case it may not be increased since sublimation refining of the compound cannot be easily performed by an increase in molecular weight caused by the above increase of the condensed rings.

On the other hand, it is believed that in the condensed ring 3, since the wavelength is significantly increased by an increase of the condensed ring corresponding to one benzene ring, a longer wavelength than that for the green light emission is obtained.

The reason for this is that the condensed ring 3 has an anthracene ring as a partial structure in the condensed ring as shown below.

However, when such an anthracene ring is present as the partial structure, regions, such as the anthracene 9- and 10-positions, which have poor resistance against oxidation and inferior chemical stability are present in the molecule.

Condensed Ring 3

Anthracene Ring

Anthracene 9-position

Anthracene 10-position

For a light emitting material which repeatedly performs excitation and light emission relaxation in an organic light emitting element, in one case a material having such a low stable region may not be provided.

Since the BTIPy ring according to aspects of the present invention has not such an anthracene-ring partial structure, the main skeleton has high oxidation resistance and high chemical stability.

In addition, since the calculated oscillator strength value of BTIPy according to aspects of the present invention is high as compared to that of each of the other condensed rings in Table 1, the main skeleton can be expected to have a high fluorescence quantum yield.

As described above, a condensed polycyclic compound having the BTIPy ring according to aspects of the present invention as the main skeleton is expected to exhibit the green light emission and to have a high chemical stability and a high fluorescence quantum yield.

In addition, if the above condensed polycyclic compound is used as a guest material of a light emitting layer of an organic light emitting element, a long-life and highly efficient light emitting element having a high green color purity can be obtained.

By the way, when the two diastereomers, BTIPy(a) and BTIPy(b), in Table 1 are compared to each other, the calculated values of the S1 energy are approximately equivalent to each other, and the calculated values of the oscillator strength are also approximately equivalent to each other; hence, the difference in terms of material physical properties between the condensed polycyclic compounds represented by the general formulas [1] and [2] according to aspects of the present invention is not hardly present.

Hence, even if a mixture between the condensed polycyclic compounds represented by the general formulas [1] and [2] according to aspects of the present invention is used at an arbitrary ratio, the properties obtained by using BTIPy as the main skeleton are not changed, and approximately uniform material physical properties can be obtained.

In addition, the condensed polycyclic compounds according to aspects of the present invention represented by the general formulas [1] and [2] may have a straight or branched alkyl group having 1 to 4 carbon atoms as the substituents $R_1$ to $R_{10}$.

When the alkyl substituent is contained, since the alkyl substituent functions as an electron donating group, the HOMO level becomes shallower rather than that of an unsubstituted compound. In other words, it may also be said that the ionization potential is decreased.

In addition, the alkyl substituent functions as a steric hindrance group which decreases the intermolecular interaction and can reduce the intermolecular stack between the condensed polycyclic groups and that between the condensed polycyclic compound and other compounds such as a host material.

When the condensed polycyclic compound according to aspects of the present invention is used as a guest material of a light emitting layer of an organic light emitting element, the concentration quenching is suppressed by the reduction in the intermolecular stack as described above, and hence, a high light emitting efficiency can be obtained.

Furthermore, since the reduction in the intermolecular stack decreases the sublimation temperature of the condensed polycyclic compound, thermal decomposition caused by overheating at the time of sublimation refining can also be prevented.

However, the straight chain or branched alkyl group having 1 to 4 carbon atoms as the substituents $R_1$ to $R_{10}$ is merely an auxiliary group and is used only for fine adjustment without significantly changing the physical properties of the condensed polycyclic compound according to aspects of the present invention.

In addition, the condensed polycyclic compounds according to aspects of the present invention represented by the general formulas [1] and [2] may have a substituted or unsubstituted aromatic hydrocarbon group having 6 to 22 carbon atoms.

When the aromatic hydrocarbon group as described above is introduced into the BTIPy main skeleton as a substituent, a π conjugated length of the condensed polycyclic compound molecule is increased, and the light emitting wavelength is increased.

However, since the number of carbon atoms of the aromatic hydrocarbon group functioning as a substituent is 22 or less, the π conjugation thereof is sufficiently small as compared to that of the BTIPy main skeleton, and the wavelength is not significantly increased so as to exceed the wavelength region of the green light emission.

Therefore, the aromatic hydrocarbon substituent is used for fine adjustment of the light emitting wavelength of the condensed polycyclic compound according to aspects of the present invention.

In particular, as shown in the general formulas [3] and [4], $R_3$ and $R_4$ of the condensed polycyclic compounds according to aspects of the present invention represented by the general formulas [1] and [2] may each be a substituted or unsubstituted phenyl group.

It is found that since the calculated value of the S1 energy of BTIPy(b) in Table 1 is approximately equivalent to that of the example compound 201(b), even if phenyl groups are introduced into the positions corresponding to the substituents $R_3$ and $R_4$ of the BTIPy main skeleton, the light emitting wavelength is hardly increased.

The reason for this is that since the hydrogen atom at the α position of the phenyl substituent and the hydrogen atom on the BTIPy ring stereochemically repel each other as shown below, the phenyl substituent is arranged approximately orthogonal to the BTIPy ring, and the π conjugation on the BTIPy ring does not extend to the phenyl substituent.

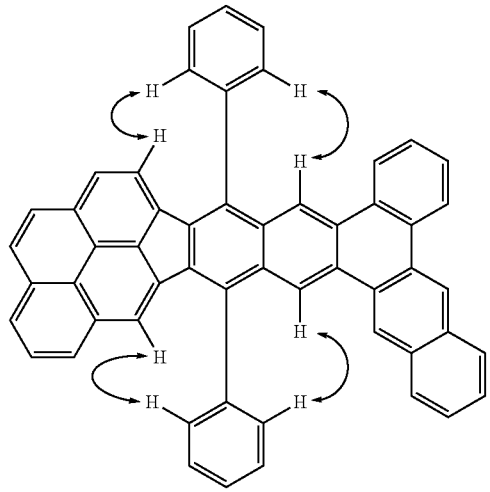 [SMILES: c1ccc(-c2c3c(c(-c4ccccc4)c4cc5c6cc7ccccc7cc6c6ccccc6c5cc24)-c2cc4cccc5ccc6ccc-3c2c6c54)cc1]

In addition, the phenyl substituent arranged orthogonal to the BTIPy main skeleton functions as a steric hindrance group which reduces the intermolecular interaction as in the case of the alkyl group described above and has an effect of reducing the intermolecular stack.

Therefore, in the condensed polycyclic compounds represented by the general formulas [3] and [4] according to aspects of the present invention, the intermolecular stack is reduced while the green light emission derived from the BTIPy main skeleton is maintained, and if this condensed polycyclic compound is used as a guest material of a light emitting layer of an organic light emitting element, highly efficient light emission having a high green color purity can be obtained.

(Example of Condensed Polycyclic Compound According to Aspects of the Present Invention)

Examples of particular structural formulas of the condensed polycyclic compound according to aspects of the present invention will be shown. An example compound 101 (a) and an example compound 101(b) are in a diastereomeric relationship, and the other example compounds are also in the same relationship as described above.

In addition, a mixture of the example compound 101(a) and the example compound 101(b) is called an example compound 101, and the other example compounds are also called in the same manner as described above.

101(a)
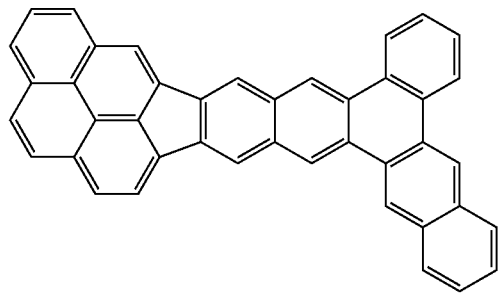
102(a)
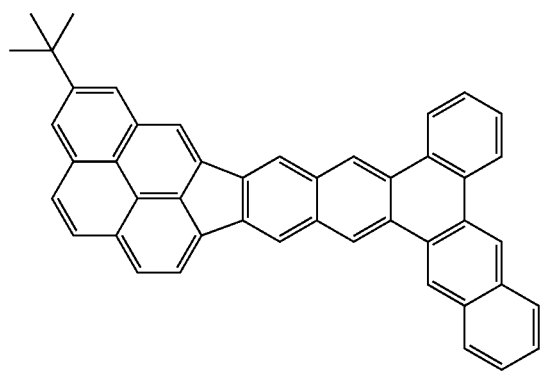
103(a)
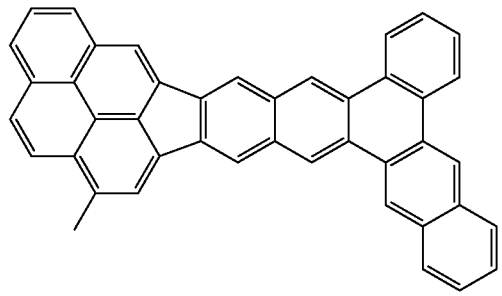
101(b)
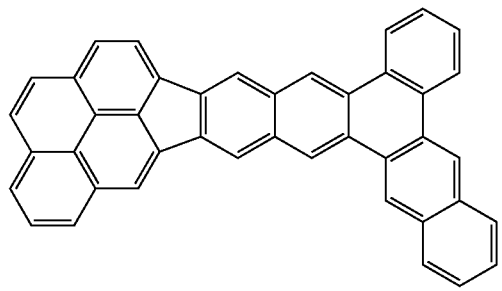
102(b)
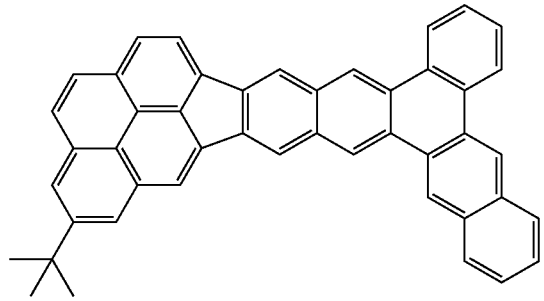
103(b)
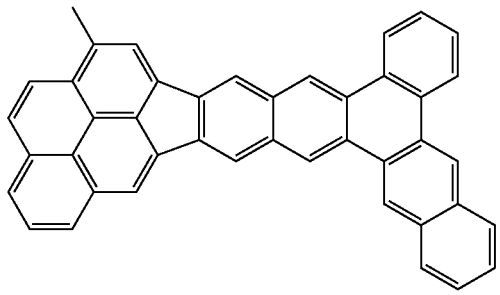
104(a)
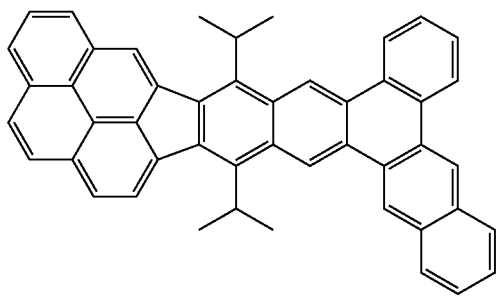
105(a)
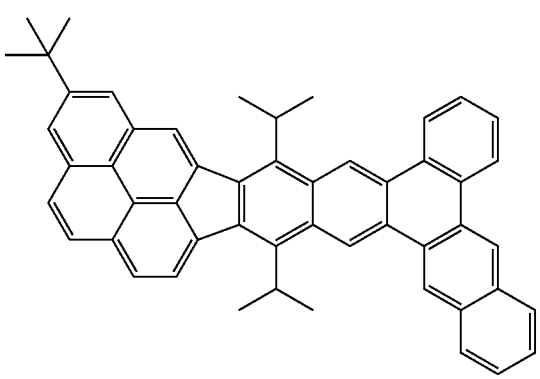
106(a)
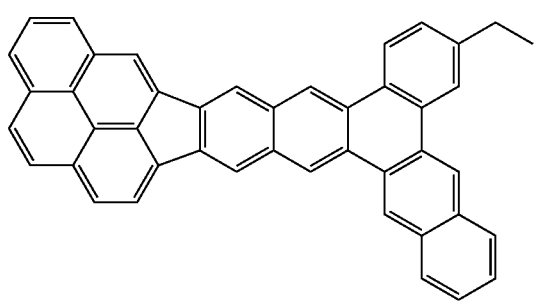
104(b)
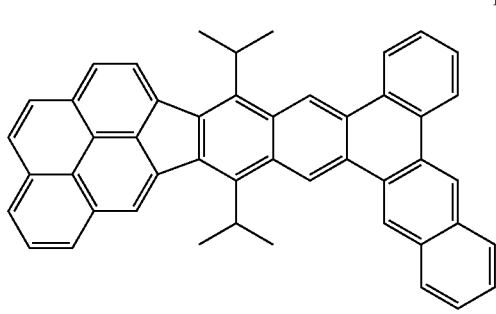

-continued
105(b)
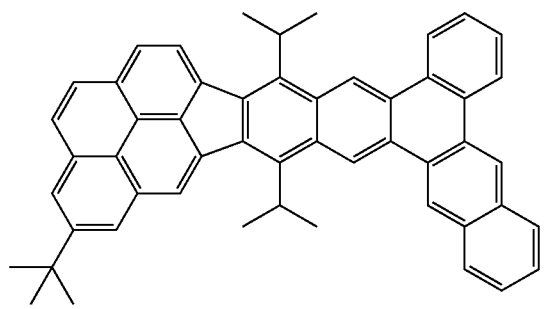
106(b)
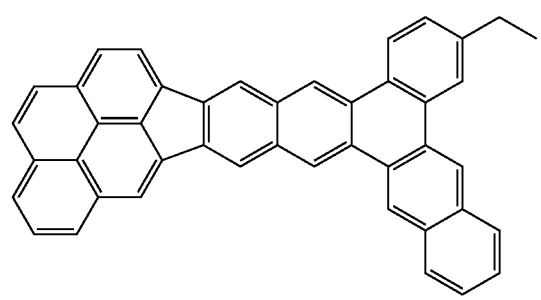
107(a)
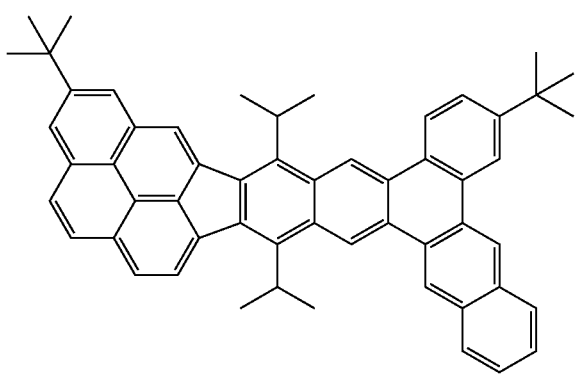
108(a)
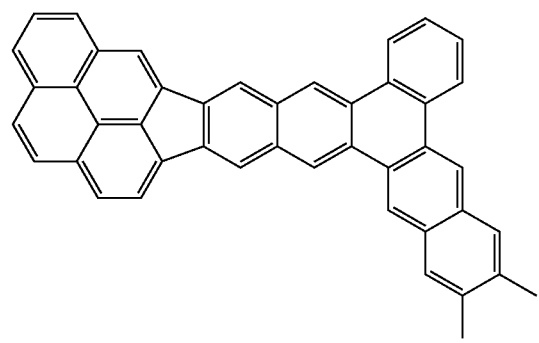
-continued
109(a)
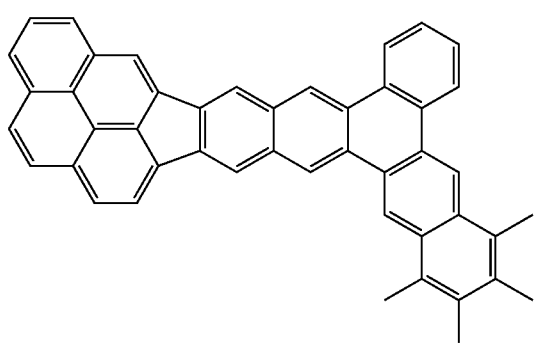
107(b)
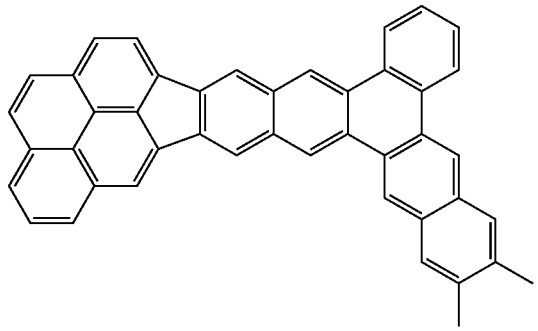
108(b)
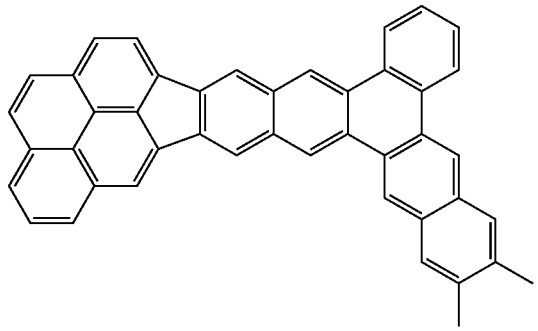
109(b)
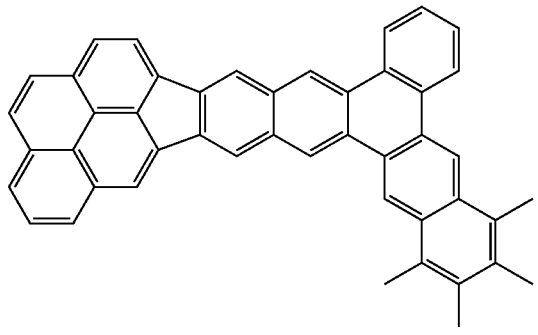

201(a)
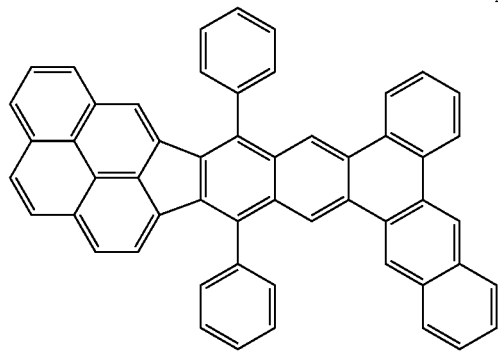
202(a)
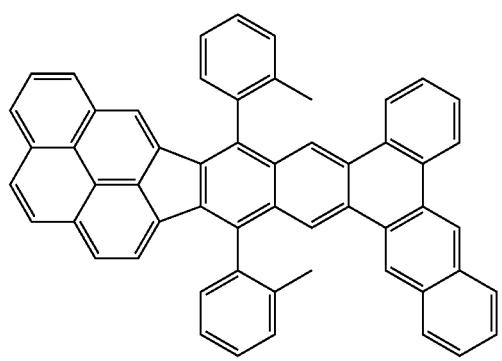
203(a)
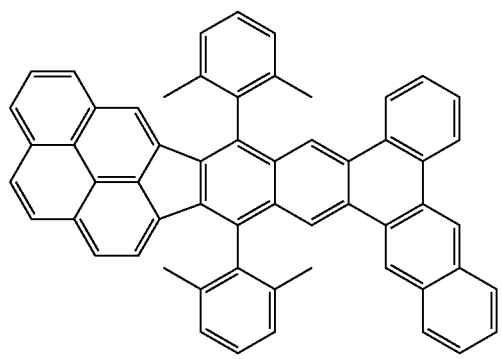
201(b)
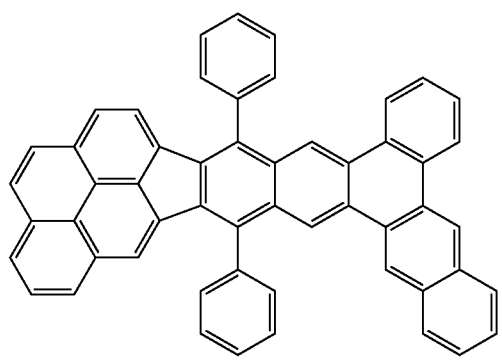
202(b)
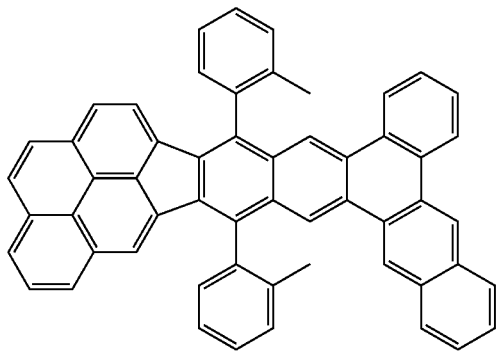
203(b)
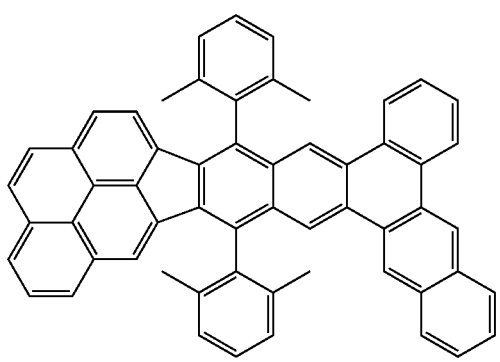
204(a)
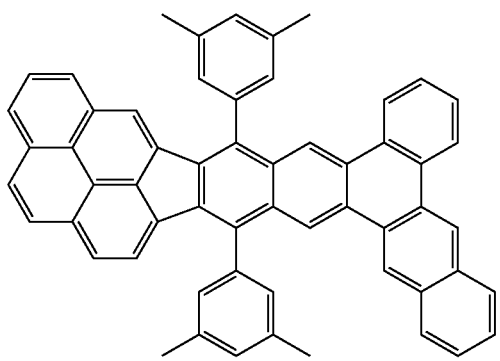
205(a)
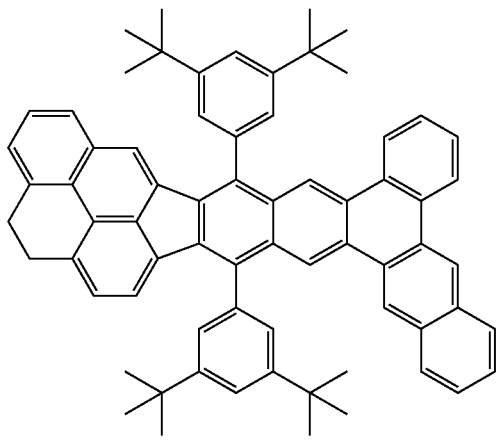

206(a)
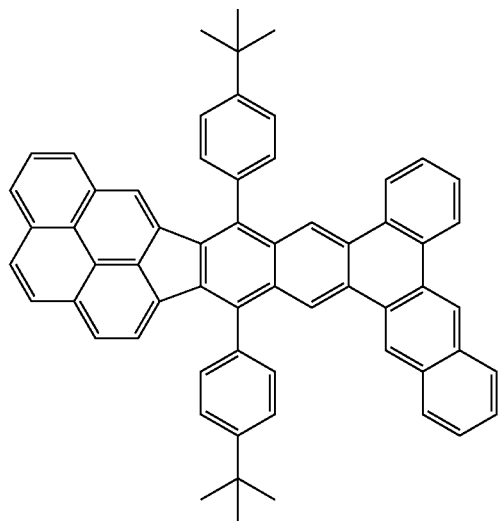
206(b)
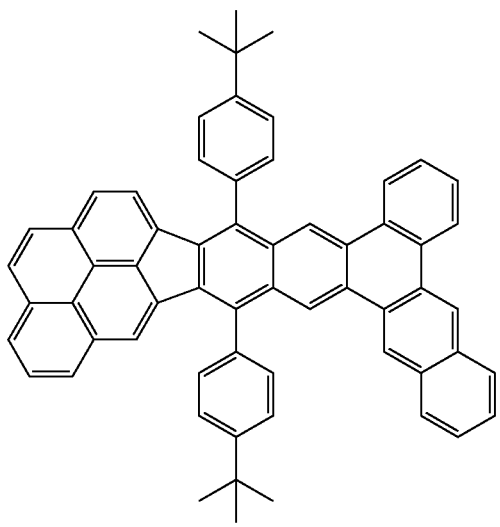
204(b)
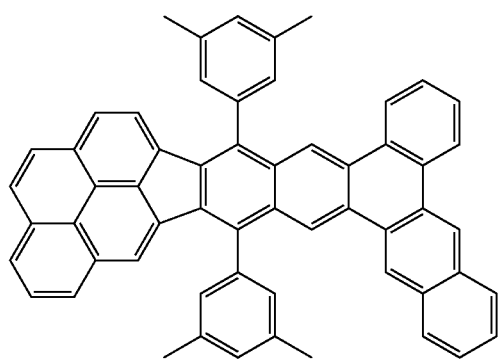
207(a)
205(b)
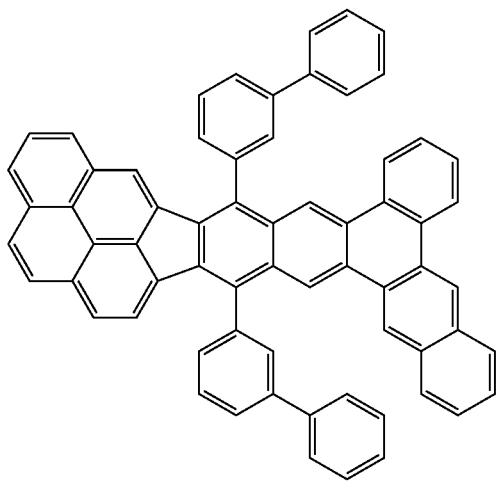
208(a)

209(a)
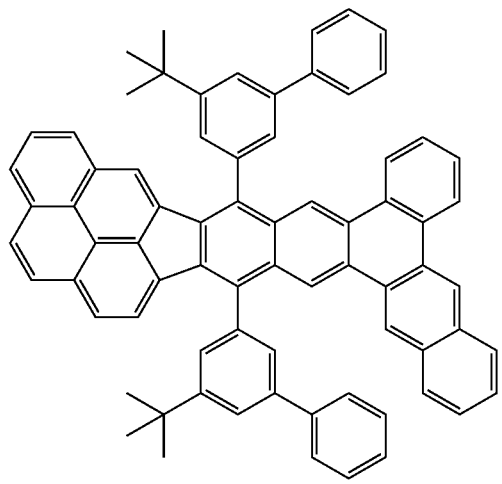
207(b)
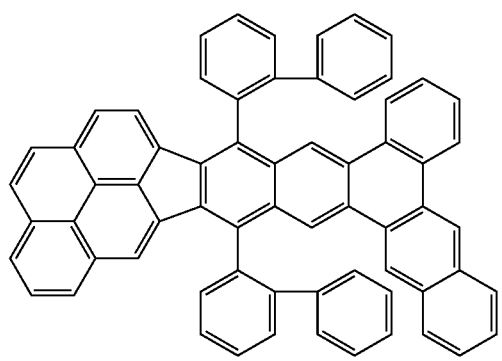
209(b)
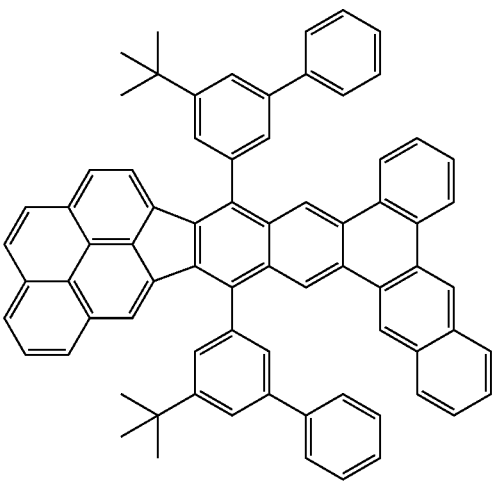
210(a)
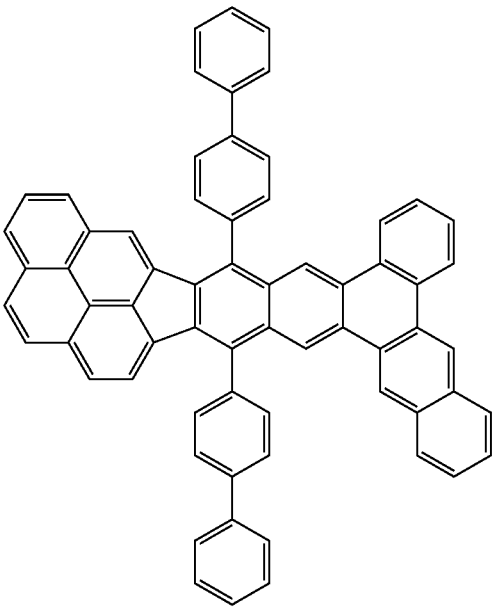
208(b)
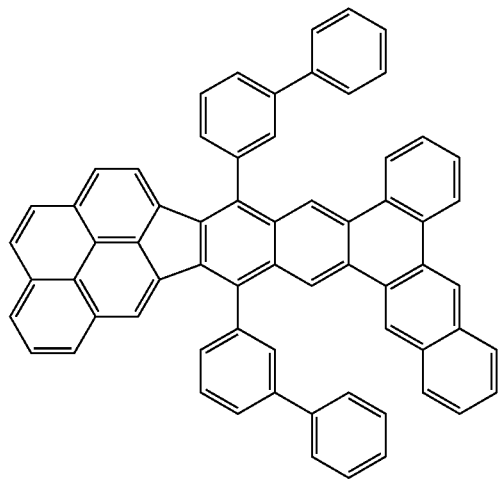

210(b)
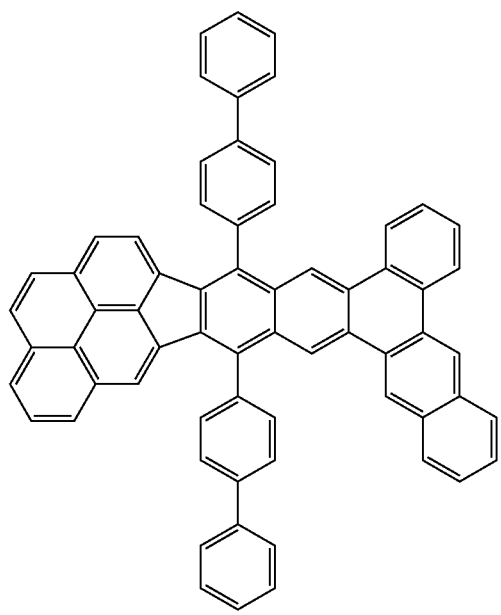
211(a)
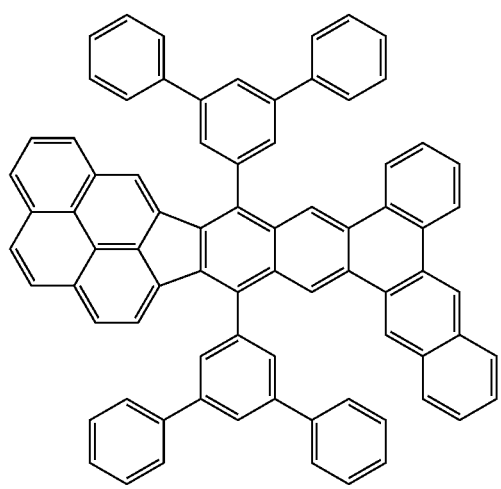
211(b)
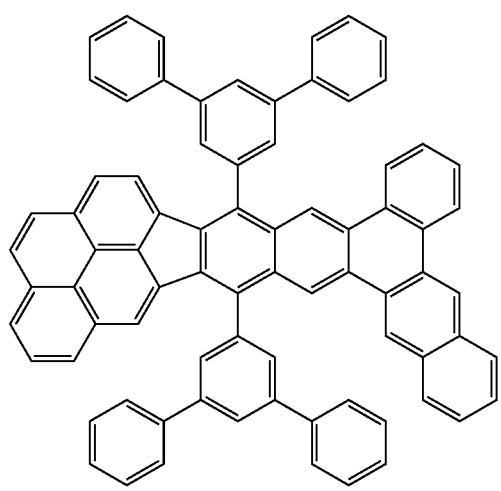
301(a)
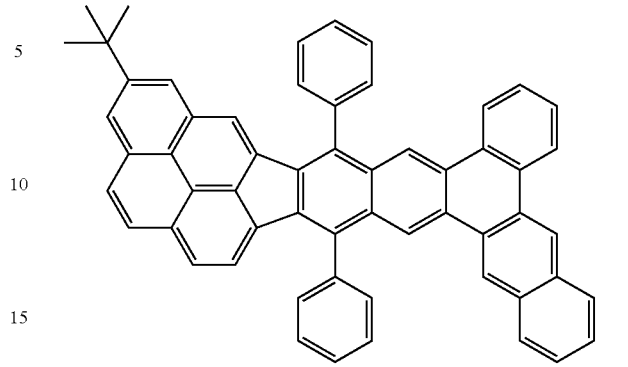
302(a)
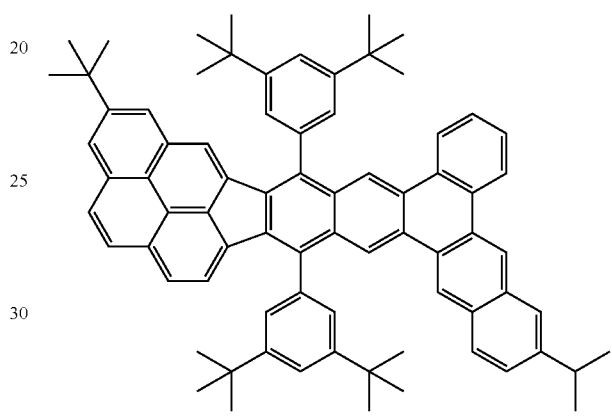
303(a)
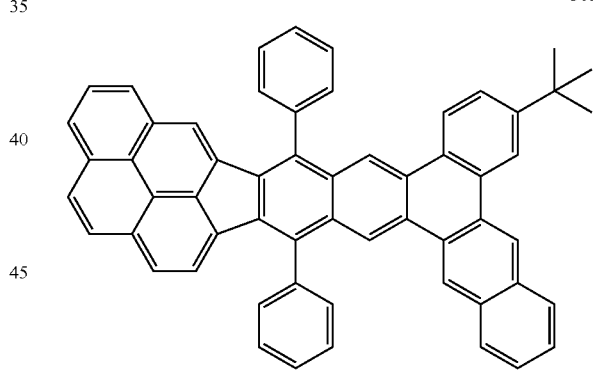
301(b)
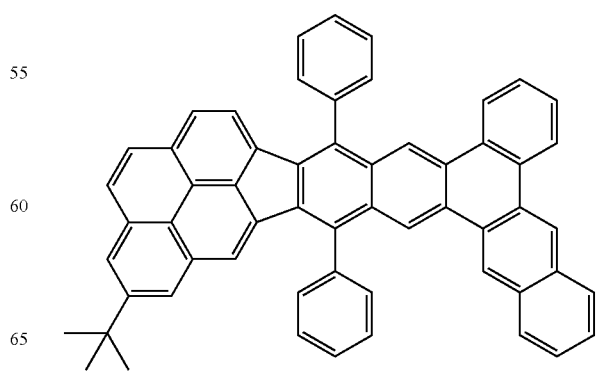

302(b)
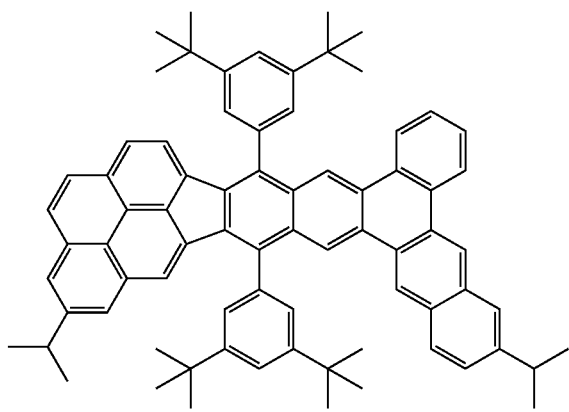
402(a)
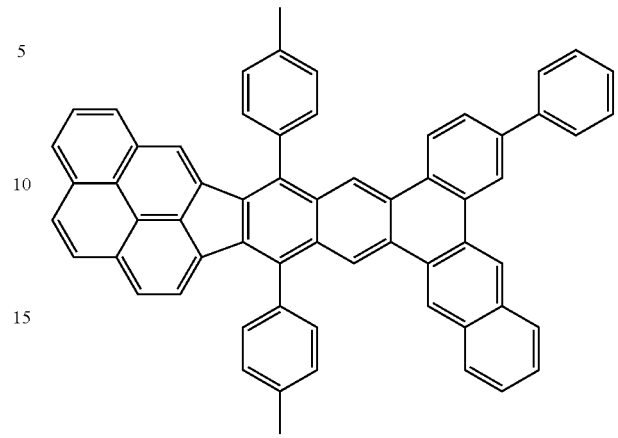
303(b)
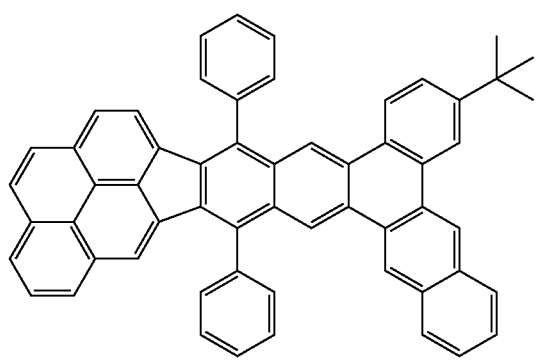
403(a)
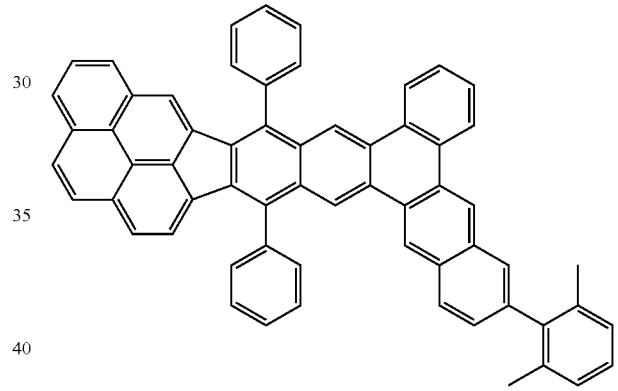
401(a)
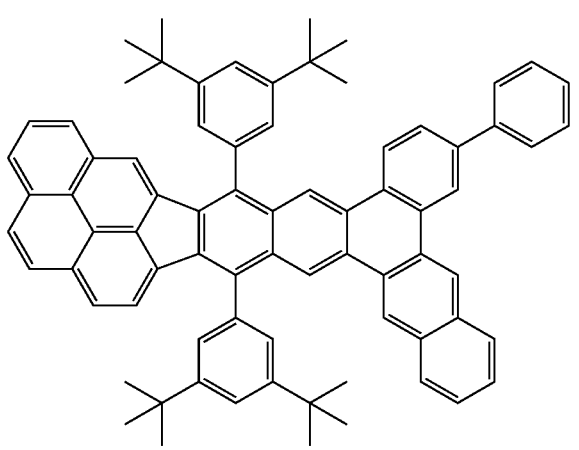
401(b)
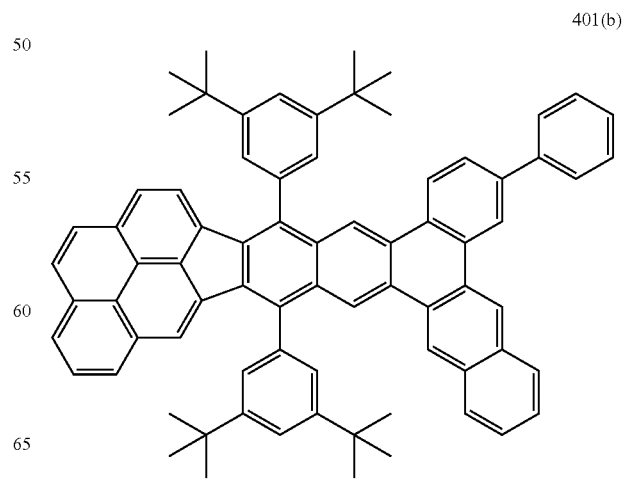

-continued
402(b)
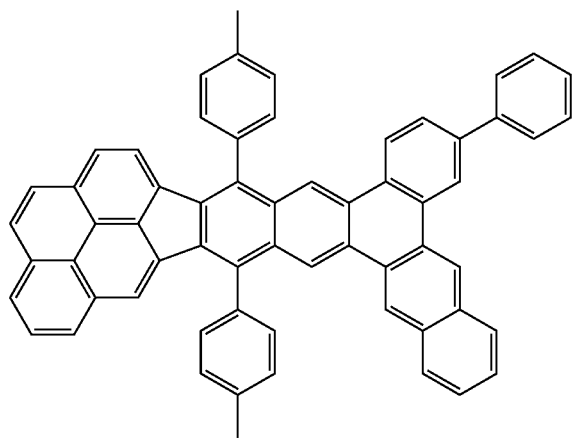
403(b)
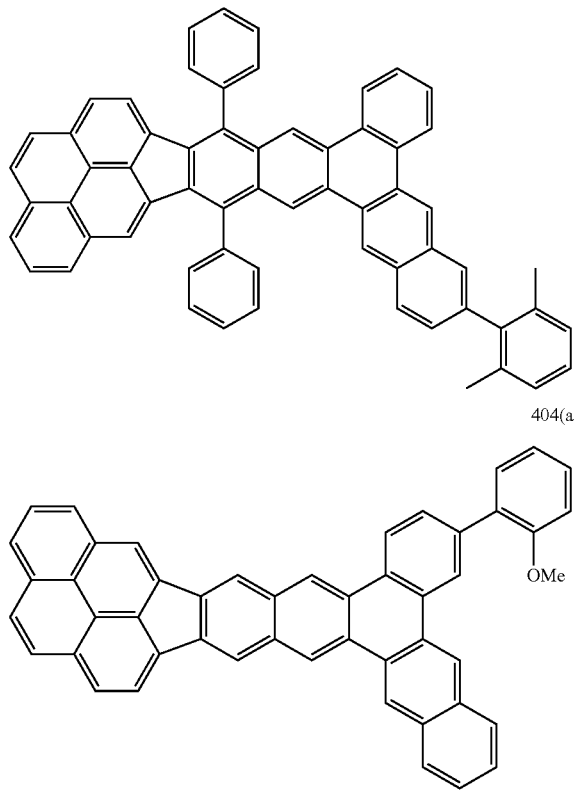
404(a)
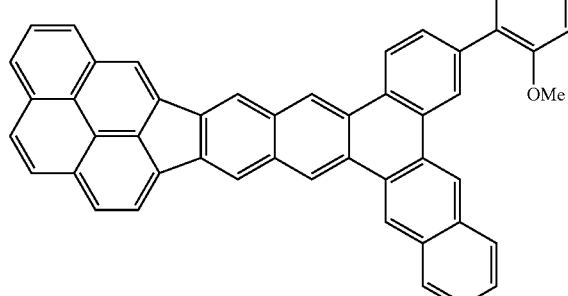
405(a)
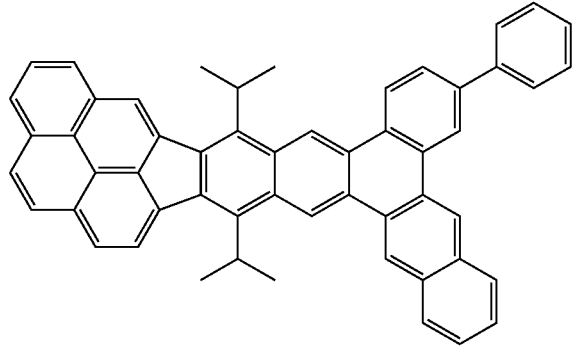
-continued
406(a)
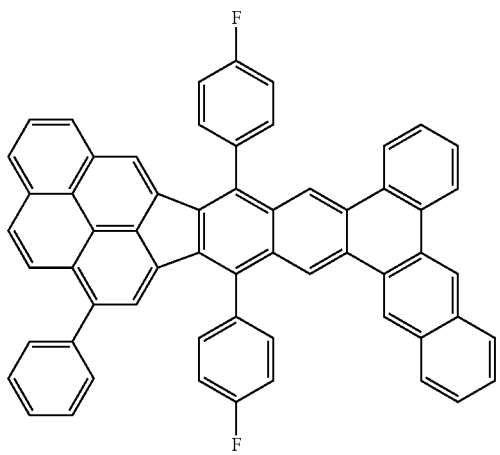
404(b)
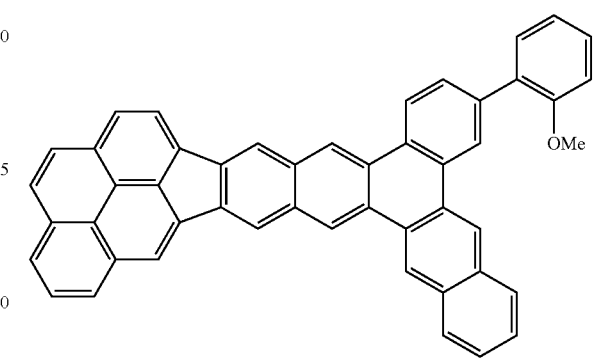
405(b)
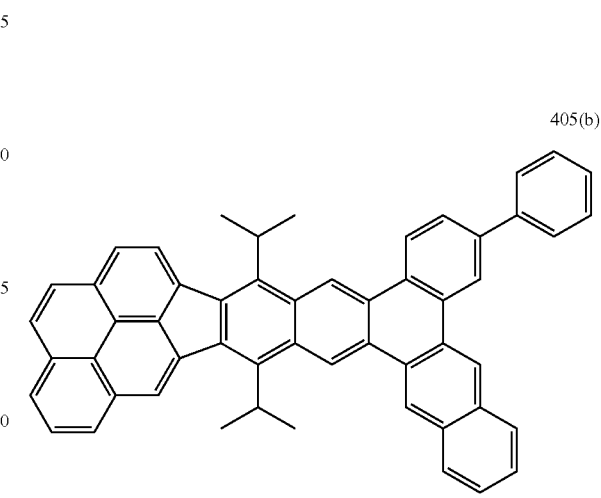

406(b)
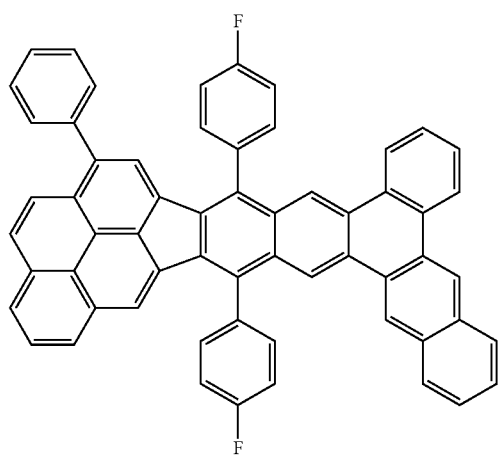
503(a)
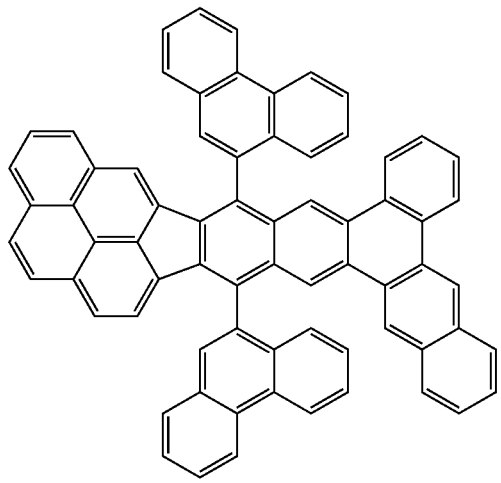
501(a)
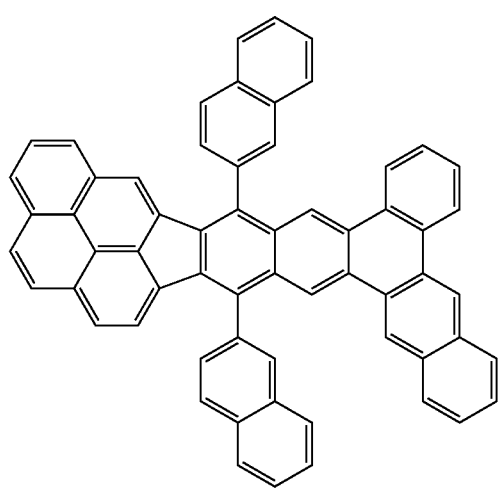
501(b)
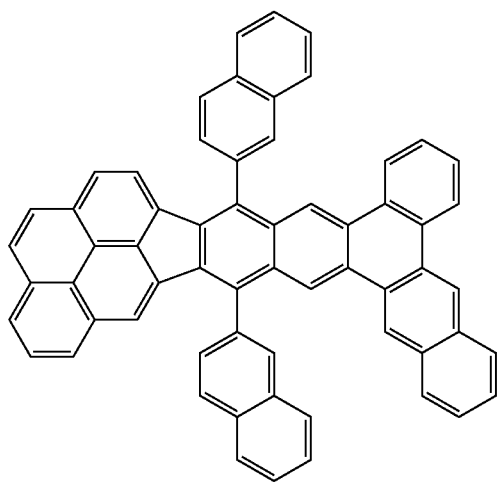
502(a)
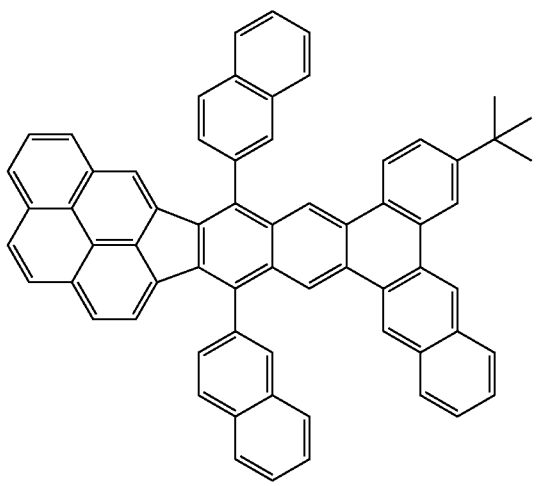
502(b)
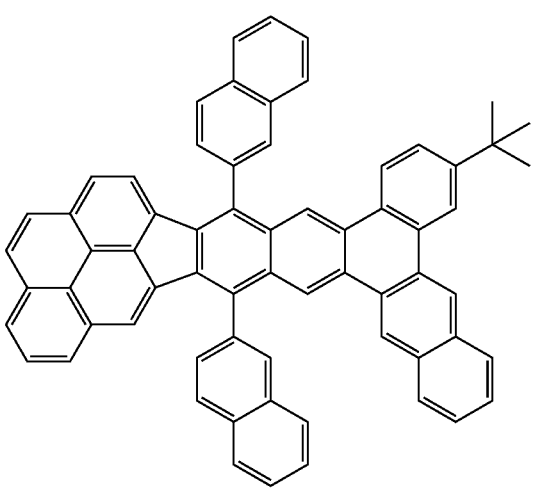

503(b)
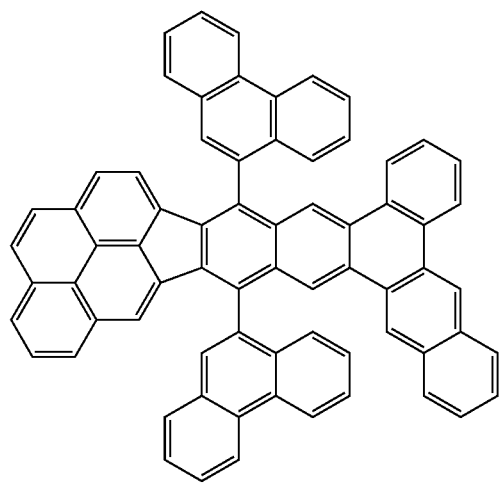
505(b)
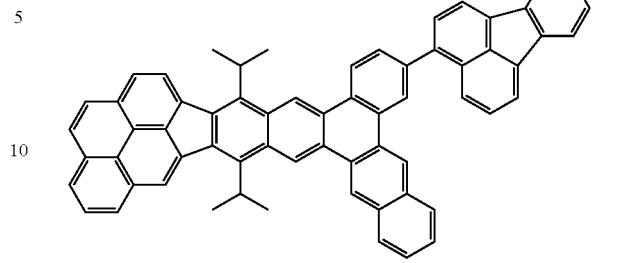
504(a)
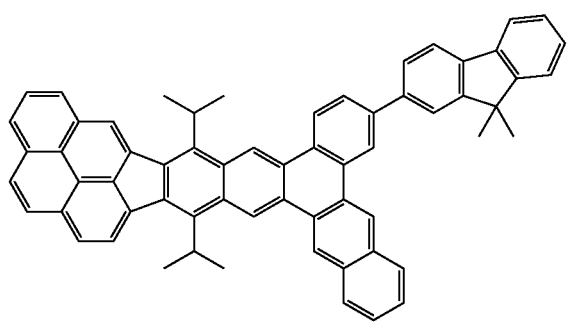
506(a)
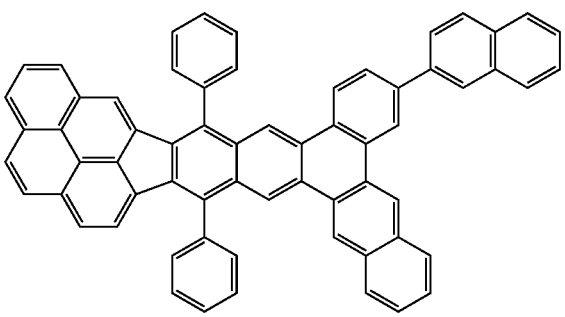
504(b)
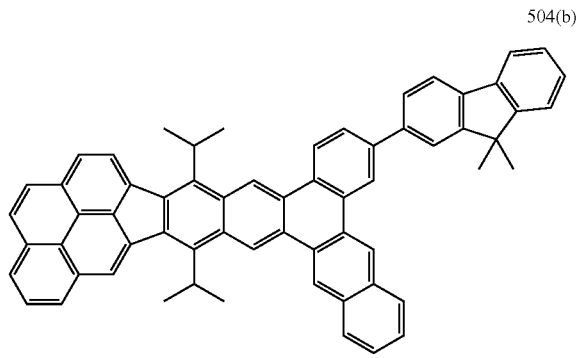
506(b)
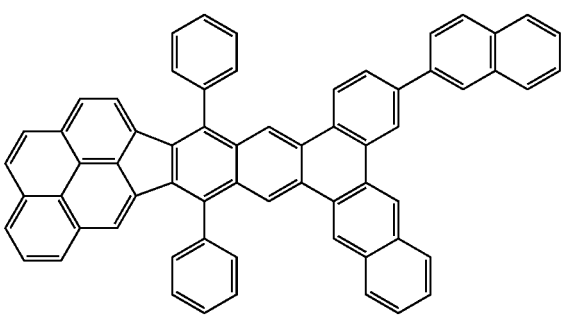
505(a)
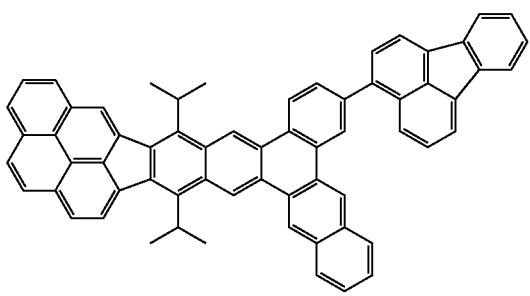
507(a)
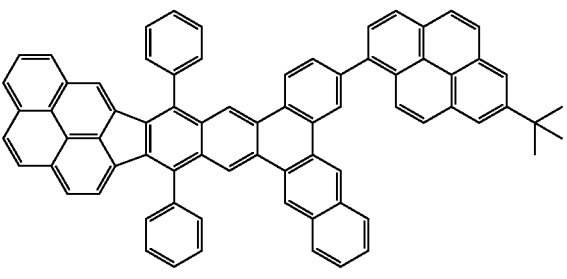

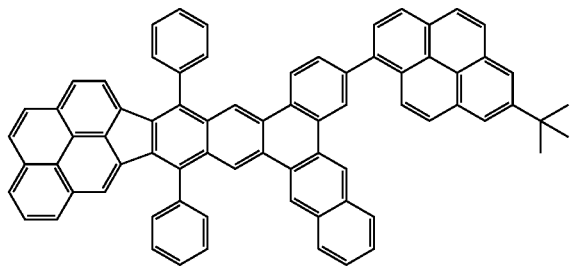

507(b)

Compounds 101 to 109 of the example compounds are a first group.

In the first group, $R_1$ to $R_{10}$ of the general formulas [1] and [2] each indicate a hydrogen atom or a straight or branched alkyl group having 1 to 4 carbon atoms.

The light emitting wavelength of each compound in the first group is equivalent to the green light emission wavelength of the BTIPy main skeleton 101, that is, the example compound 101, and since the molecular weight thereof is relatively small, sublimation refining can be easily performed.

Compounds 201 to 211 of the example compounds are a second group.

The compounds in the second group are each represented by the general formula [3] or [4] and each have only substituted or unsubstituted phenyl groups at specific positions of the BTIPy main skeleton.

By the compounds in the second group, light emission having a high green color purity derived from the BTIPy main skeleton can be obtained, and when the compound in this group is used as a guest material of a light emitting layer, highly efficient light emission can be obtained because of reduction of the intermolecular stack.

Compounds 301 to 303 of the example compounds are a third group.

The compounds in the third group each further have at least one straight or branched alkyl group having 1 to 4 carbon atoms as a substituent on the BTIPy main skeleton represented by the general formula [3] or [4].

In the compounds in the third group, the intermolecular stack is further reduced rather than that of the compound in the second group by the alkyl substituent on the BTIPy main skeleton.

Compounds 401 to 406 of the example compounds are a fourth group.

In the compounds in the fourth group, at least one of $R_1$, $R_2$, and $R_5$ to $R_{10}$ of the general formulas [1] and [2] is a substituted or unsubstituted phenyl group.

In the compounds in the fourth group, green light emission having an emission peak wavelength longer than that of the compounds in the first to the third groups by approximately 10 nm can be obtained.

Compounds 501 to 507 of the example compounds are a fifth group.

In the compounds in the fifth group, at least one of $R_1$ to $R_{10}$ of the general formulas [1] and [2] is a substituted or unsubstituted aromatic hydrocarbon group having 8 to 22 carbon atoms.

In the compounds in the fifth group, green light emission having an emission peak wavelength longer than that of the compounds in the fourth group can be obtained.

(Synthetic Method of Condensed Polycyclic Compound According to Aspects of the Present Invention)

Next, a synthetic method of the condensed polycyclic compound represented by the formula [1] or [2] according to this embodiment will be described.

The condensed polycyclic compound according to aspects of the present invention is synthesized by a Suzuki coupling reaction and a Heck reaction, which are shown in the following formula [6], from a BrCl intermediate of benzo[5,6]indeno[1,2,3-cd]pyrene obtained by a reaction shown in the following formula [5].

In this case, a diastereomeric mixture of BrCl intermediates is obtained by a Diels-Alder reaction shown in the following formula [5] using bromo chloro anthranilic acid.

In addition, this geometrical isomerism is also maintained in the following reaction shown in the formula [6], and the condensed polycyclic compound according to aspects of the present invention is obtained in the form of a mixture of diastereomers, a BTIPy(a) derivative and a BTIPy(b) derivative. The following formula [6] indicates a synthetic scheme in the case of the BTIPy(a) derivative, and the same scheme as described above may also be applied in the case of the BTIPy (b) derivative.

[5]

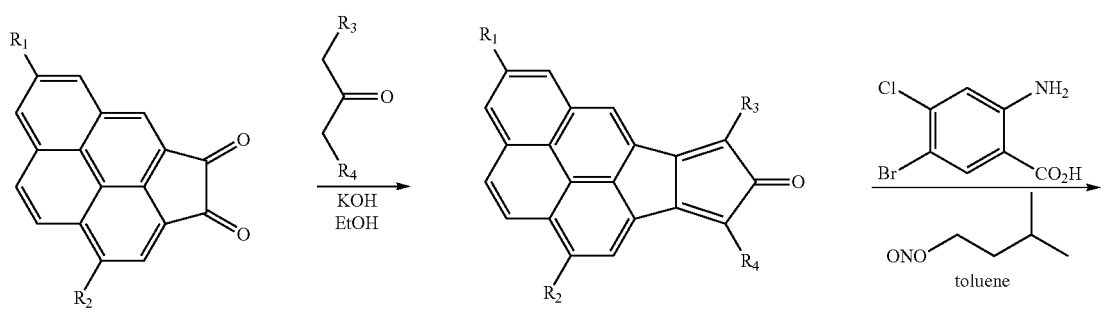

-continued
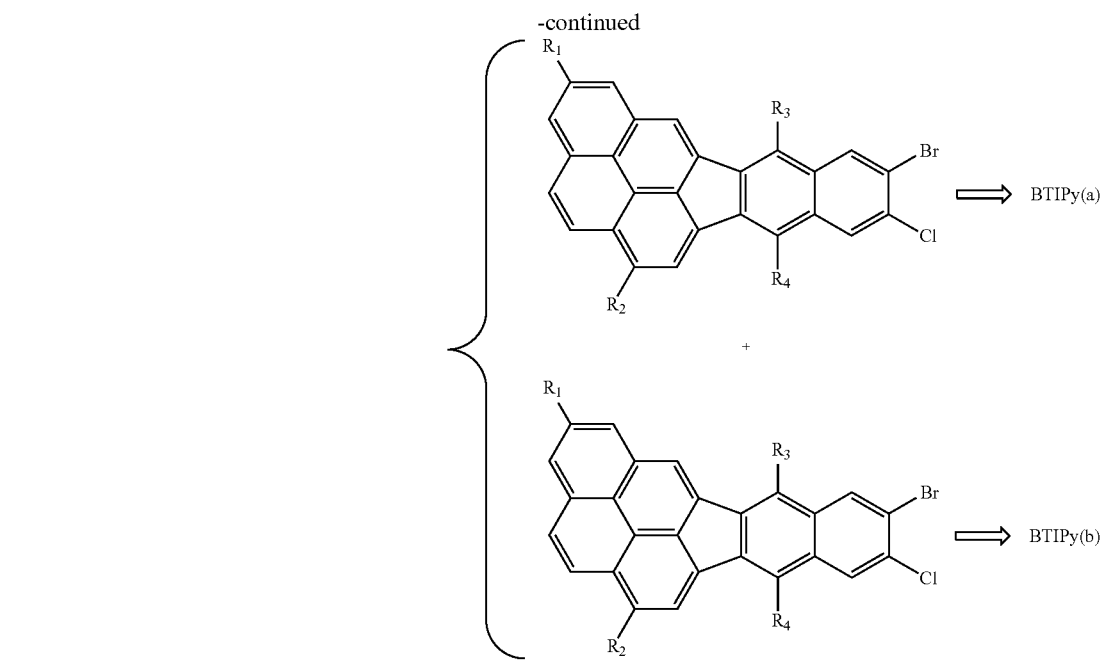
[6]
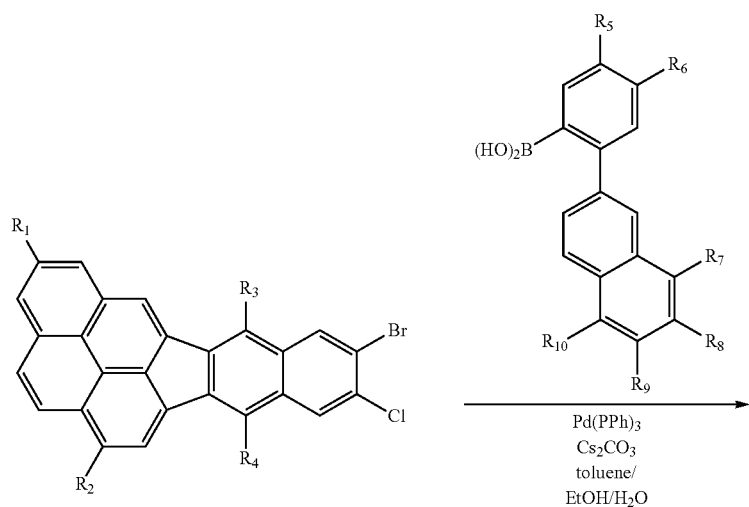
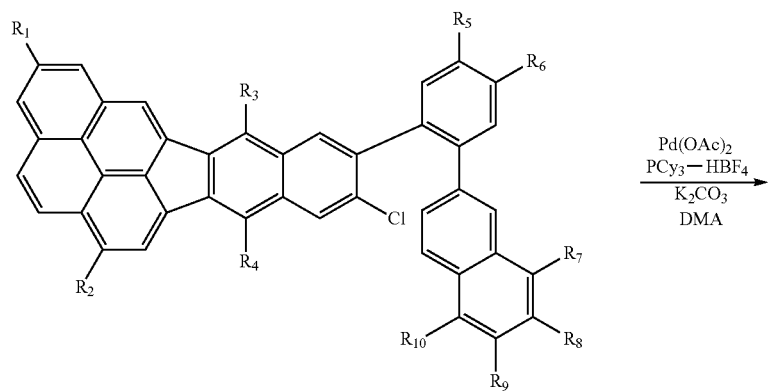

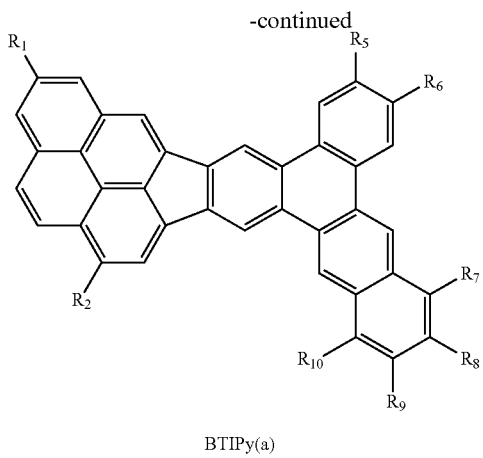

BTIPy(a)

In the condensation reaction in the formula [5], a predetermined BrCl intermediate can be obtained by appropriately selecting a diketone raw material and a ketone raw material.

Furthermore, a predetermined condensed polycyclic compound according to aspects of the present invention can be synthesized when a Suzuki coupling reaction in the formula [6] is performed by appropriately selecting this BrCl intermediate and a naphthyl phenylboronic acid compound having a substituent.

In addition, when the condensed polycyclic compound according to aspects of the present invention is used for an organic light emitting element, sublimation refining may be performed as last refining. The reason for this is that sublimation refining has a significant refining effect in purification of organic compounds.

In such sublimation refining, in general, a higher temperature is necessary as the molecular weight of an organic compound is increased, and in this case, for example, thermal decomposition is liable to occur by this high temperature.

Hence, the organic compound used for an organic light emitting element may have a molecular weight of 1,000 or less so that sublimation refining can be performed without excessive heating.

(Organic Light Emitting Element According to the Aspects of the Present Invention)

Next, an organic light emitting element according to aspects of the present invention will be described.

The organic light emitting element according to aspects of the present invention is a light emitting element at least including an anode, a cathode, which are a pair of electrodes facing each other, and at least one organic compound layer arranged between the electrodes. A layer among the organic compound layers which contains a light emitting material is a light emitting layer.

In addition, in the organic light emitting element according to aspects of the present invention, the above organic compound layer contains the condensed polycyclic compound represented by the general formula [1] or [2].

As an element structure of the organic light emitting element according to aspects of the present invention, a multilayer element structure in which the following layers are successively laminated on a substrate may be mentioned.
(1) anode/light emitting layer/cathode
(2) anode/hole transport layer/light emitting layer/electron transport layer/cathode
(3) anode/hole transport layer/light emitting layer/electron transport layer/electron injection layer/cathode
(4) anode/hole injection layer/hole transport layer/light emitting layer/electron transport layer/cathode
(5) anode/hole injection layer/hole transport layer/light emitting layer/electron transport layer/electron injection layer/cathode
(6) anode/hole transport layer/electron block layer/light emitting layer/hole block layer/electron transport layer/cathode However, these examples of the element structure are each a very simple basic element structure, and the structure of the organic light emitting element using the compound according to aspects of the present invention is not limited to those mentioned above.

Various layer structures can be formed, and for example, an insulating layer may be provided at an interface between the electrode and the organic compound layer, an adhesive layer or an interference layer may be provided, the electron transport layer or the hole transport layer may be formed from two layers having different ionization potentials, and/or the light emitting layer may include two layers formed from different light emitting materials.

As an element configuration of the above structures, a so-called bottom emission system in which light is extracted from an electrode at a substrate side, a so-called top emission system in which light is extracted from a side opposite to the substrate, and a dual emission system in which light is extracted from both surface sides may be used.

In addition, among the above element structures, the structure (6) which has both the electron block layer and the hole block layer may be used. Since both carriers, holes and electrons, can be confined in the light emitting layer by the structure (6), an element having a high light emitting efficiency without carrier leakage can be obtained.

The compound according to aspects of the present invention is primarily used for the light emitting layer of the organic light emitting element. In this case, the light emitting layer may include a plurality of types of components, and the components can be classified into a primary component and accessory components.

The primary component is a compound, the weight ratio of which is highest among all the compounds forming the light emitting layer, and can also be called a host material. The accessory components are compounds other than the primary component and can be called a guest (dopant) material, a light emission assistant material, and a charge injection material.

In this case, the guest material is a compound responsible for primary light emission in the light emitting layer. On the other hand, the host material is a compound present as a matrix in the light emitting layer to surround the guest material and is primarily responsible to transport carriers and impart excitation energy to the guest material.

The light emission assistant material is a compound which has a weight ratio lower than that of the host material in the light emitting layer, which assists light emission of the guest material, and which is also called a second host material.

The concentration of the guest material to the host material is in a range of 0.01 to 50 percent by weight on the basis of the total weight of the components of the light emitting layer and may be in a range of 0.1 to 20 percent by weight.

In addition, in order to prevent the concentration quenching, the concentration of the guest material may be 10 percent by weight or less.

The guest material may be included uniformly in the whole layer formed of the host material or may be included therein to form a concentration gradient, or the guest material may be included partially in a specific region to form a region of a host material layer containing no guest material.

The condensed polycyclic compound according to aspects of the present invention may be used as the guest material of the light emitting layer.

Although the light emission color of the condensed polycyclic compound according to aspects of the present invention is not particularly limited in this case, a green light emitting material may be selected so that the maximum emission peak wavelength of a light emitting element using the above material as a guest material of a light emitting layer is in a range of 500 to 540 nm.

When the condensed polycyclic compound according to aspects of the present invention is used as the guest material of the light emitting layer, as the host material thereof, a compound having S1 energy higher than that of the condensed polycyclic compound according to aspects of the present invention is used.

In this case, the excitation energy of the host material excited by carrier recombination is efficiently transferred to the guest material, and light emission from the guest material can be obtained with high efficiency.

Furthermore, as the host material of the light emitting layer, an aromatic hydrocarbon compound (molecule) formed only from carbon atoms and hydrogen atoms may be provided. In this case, a light emitting device having high drive durability and a small degradation in luminance is obtained.

Since the host material of the light emitting layer is responsible for carrier conduction as radical cations or radical anions in the light emitting layer and is also responsible to impart excitation energy to the guest material when excited, in such a high energy state, a large load is applied to the host material.

Hence, since having a chemical stability superior to that of a compound having a hetero atom, such as an oxygen atom and/or a nitrogen atom, an aromatic hydrocarbon compound may be used as the host material of the light emitting layer.

In addition, in order to assist conduction of excitons and/or carriers, the light emitting layer may contain a plurality of host materials and may also contain a light emission assistant material different from the guest material.

Although examples of compounds used as the host material of the light emitting layer according to aspects of the present invention will be shown below, the present invention is not limited thereto.

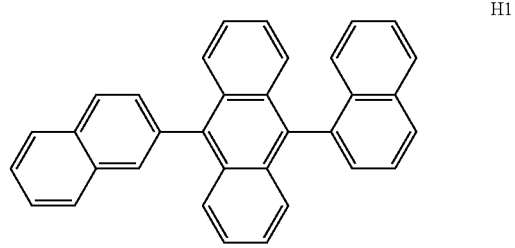

H1

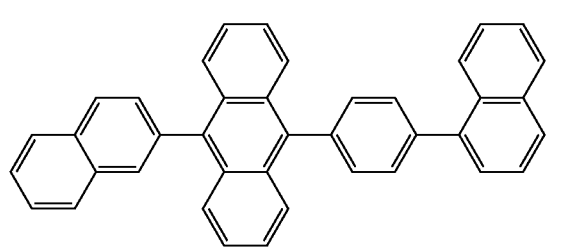

H2

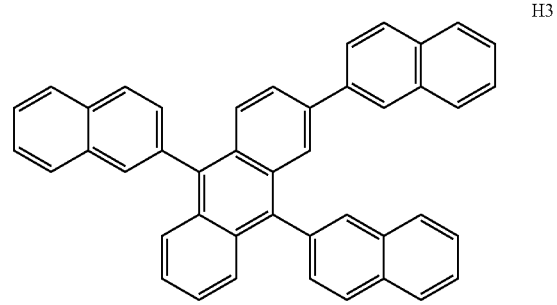

H3

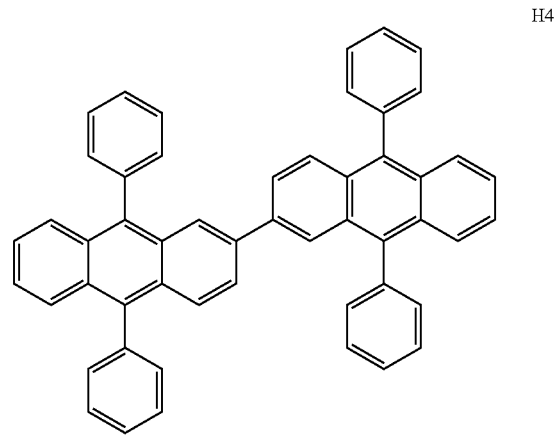

H4

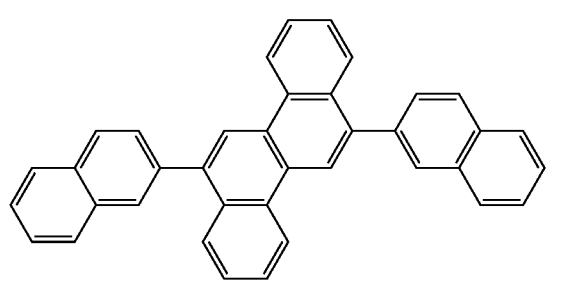

H5

H6
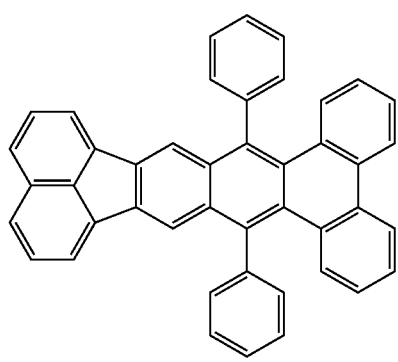
H7
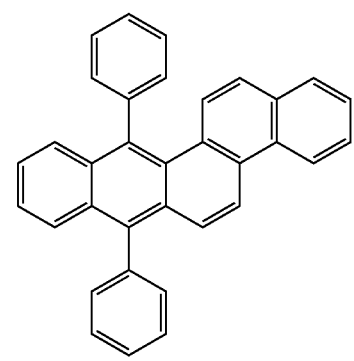
H8
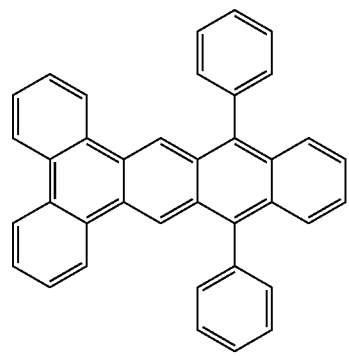
H9
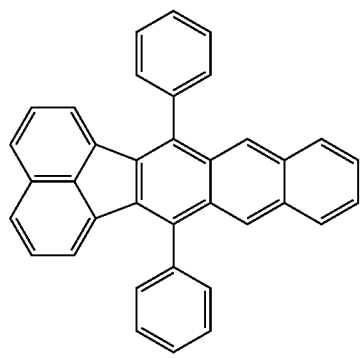
H10
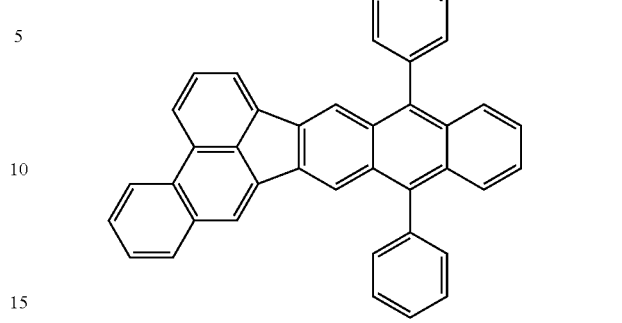
H11
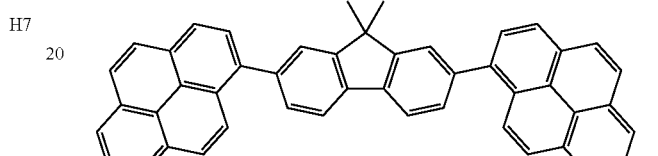
H12
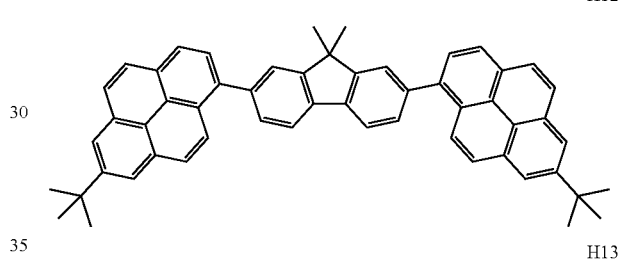
H13
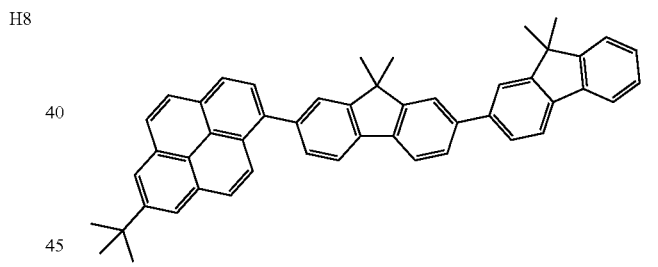
H14
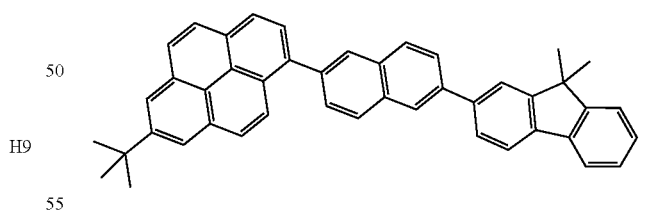
H15
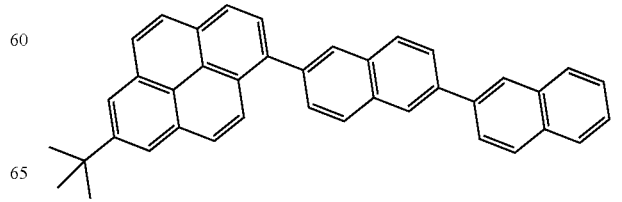

H16

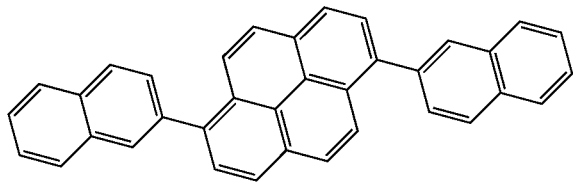

Among those compounds, H9 and H10, each of which is an example of a host material having a fluoranthene structure in its molecule, and H11 which is an example of a host material having a pyrene skeleton may be provided.

When the light emitting layer is formed from the condensed polycyclic compound according to aspects of the present invention in combination with another light emitting material, an organic light emitting element which emits white light can also be provided.

That is, since the condensed polycyclic compound according to aspects of the present invention is primarily a green light emitting material, when a light emitting layer is appropriately formed from the above condensed polycyclic compound in combination with light emitting materials which emit light other than green, such as blue, yellow, orange, and red, white light emission can be obtained.

In particular, as the light emitting layer of the organic light emitting element, at least two types of light emitting materials having different emission colors may be contained in one light emitting layer (single light emitting layer type), or a plurality of light emitting layers having emission colors different from each other, each layer being formed from a single light emitting material or a plurality of light emitting materials, may be laminated to each other (laminated light emitting layer type).

In this case, in each light emitting layer, the light emitting material may be used as the guest material of the light emitting layer together with a host material thereof, and in the case of the laminated light emitting layer type, host materials of the light emitting layers may be the same or different from each other.

FIG. 1 is a schematic cross-section view of one example of a laminated light emitting layer type element.

This organic light emitting element has an element structure in which an anode 1, a hole injection layer 2, a hole transport layer 3, a blue light emitting layer 4, a green light emitting layer 5, a red light emitting layer 6, an electron transport layer 7, an electron injection layer 8, and a cathode 9 are laminated in this order on a substrate of a glass or the like.

In the laminated light emitting layer type, a white light emitting layer having a three-layer structure in which for example, a blue light emitting layer containing a blue light emitting material, a green light emitting layer containing a green light emitting material, and a red light emitting layer containing a red light emitting material are sequentially laminated from an anode side may be used.

The organic light emitting element which emits white light according to this embodiment has a plurality of light emitting layers, and at least one of the light emitting layers contains the condensed polycyclic compound according to aspects of the present invention and emits green light.

It may also be said that the plurality of light emitting layers forms a light emitting portion.

When an organic light emitting element which emits white light is obtained, although the blue light emitting material is not particularly limited, a light emitting material having a fluoranthene skeleton or an anthracene skeleton may be provided.

In addition, although the red light emitting material is not particularly limited, a light emitting material having a fluoranthene skeleton or a pyrene skeleton and an iridium complex may be provided.

The other light emitting layers among the plurality of light emitting layers are each a light emitting layer which emits light other than green light, and a light emitting element which emits white light can be obtained when a plurality of types of light emitted from the light emitting layers are mixed together.

In this case, the lamination order of three colors, blue, green, and red, from the anode side is not particularly limited. Alternatively, a white light emitting layer having a two-layer structure in which a blue light emitting layer containing a blue light emitting material and a yellow light emitting layer are laminated to each other may be formed.

In this case, the yellow light emitting layer may have only one yellow light emitting material or may contain a plurality of light emitting materials (such as a green light emitting material and a red light emitting material) in one layer.

In the laminated light emitting layer type, in each color light emitting layer, high degree of design freedom in view of selection of emission colors of light emitting materials, combination therebetween, the lamination order, the concentration of the light emitting material, the thickness thereof, and the like can be obtained, and carrier balance can be optimized in each color light emitting layer.

Hence, the emission intensity of each emission color can be optimized, and excellent white light emission can be obtained.

In addition, the light emitting layers may not be restricted to be laminated to each other but may also be arranged side by side. The light emitting layers arranged side by side are each arranged so as to be in contact with the hole transport layer and the electron transport layer.

In addition, the light emitting layer may also have a structure in which in a light emitting layer which emits one color light, a domain of a light emitting layer which emits color light different therefrom is formed.

In addition, in the organic light emitting element according to aspects of the present invention, optionally, currently known low molecular weight and high molecular weight materials may also be used besides the condensed polycyclic compound according to aspects of the present invention. In more particular, for example, a hole injection/transport material, a host material, a light emitting material, or an electron injection/transport material may also be used together.

Hereinafter, examples of these materials will be described.

As the hole injection/transport material, a material having a high hole mobility may be provided so that holes from the anode are easily injected and injected holes can be transported to the light emitting layer. In addition, in order to prevent degradation of film qualities, such as crystallization, in the element, a material having a high glass transition point temperature may be provided. As the low molecular weight and high molecular weight materials each having a hole injection/transport ability, for example, there may be mentioned a triarylamine derivative, an arylcarbazole derivative, a phenylenediamine derivative, a stilbene derivative, a phthalocyanine derivative, a porphyrin derivative, a poly(vinyl carbazole), a polythiophene, and other conductive polymers.

As a light emitting material primarily having a light emission function, besides the condensed polycyclic compounds according to aspects of the present invention, for example, there may be mentioned an aromatic hydrocarbon compound (such as a fluorene derivative, a naphthalene derivative, a pyrene derivative, a perylene derivative, a tetracene derivative, an anthracene derivative, a rubrene derivative, or a fluoranthene derivative), a quinacridone derivative, a coumarin derivative, a stilbene derivative, an organic aluminum complex, such as tris(8-quinolinolato)aluminum, an organic beryllium complex, a phosphorescence light emitting material (such as an iridium complex, a platinum complex, or an osmium complex), and a polymer derivative, such as a poly (phenylene vinylene) derivative, a polyfluorene derivative, or a polyphenylene derivative.

As the host material of the light emitting layer, in one case a material having a high transport ability of both types of carriers, holes and electrons, may be provided, and besides the above organic hydrocarbon compounds and the derivatives thereof, for example, there may be mentioned a carbazole derivative, a dibenzofuran derivative, a dibenzothiophene derivative, an organic aluminum complex, such as tris(8-quinolinolato)aluminum, and an organic beryllium complex.

As the electron injection/transport material, a material may be arbitrarily selected from materials in which electrons from the cathode can be easily injected and which can transport injected electrons to the light emitting layer and may also be selected in consideration, for example, of the balance with the hole mobility of the hole injection/transport material. As a material having an electron injection ability and an electron transport ability, for example, there may be mentioned an oxadiazole derivative, an oxazole derivative, a pyrazine derivative, a triazole derivative, a triazine derivative, a quinoline derivative, a quinoxaline derivative, a phenanthroline derivative, and an organic aluminum complex.

A material having a higher work function may be used as an anode material. For example, a metal itself, such as gold, platinum, silver, copper, nickel, palladium, cobalt, selenium, vanadium, or tungsten, an alloy thereof, and a metal oxide, such as tin oxide, zinc oxide, indium oxide, indium tin oxide (ITO), or indium zinc oxide, may be used. In addition, conductive polymers, such as a polyaniline, a polypyrrole, and a polythiophene, may also be used.

These electrode materials may be used alone, or at least two types thereof may also be used in combination. In addition, the anode may be formed from one layer or a plurality of layers.

On the other hand, a material having a low work function may be used as a cathode material. For example, an alkali metal such as lithium, an alkaline earth metal, such as calcium, and a metal itself, such as aluminum, titanium, manganese, silver, lead, or chromium, may be mentioned.

Alternatively, an alloy formed in combination of the above metals may also be used. For example, magnesium-silver, aluminum-lithium, and aluminum-magnesium may be used. A metal oxide, such as indium tin oxide (ITO), may also be used.

These electrode materials may be used alone, or at least two types thereof may also be used in combination. In addition, the cathode may be formed from one layer or a plurality of layers.

In the organic light emitting element according to aspects of the present invention, a layer containing the organic compound according to aspects of the present invention and a layer containing the other compound are each formed by the following method.

The organic compound layer according to this embodiment is formed by a vacuum deposition method, an ionized deposition method, a sputtering method, a plasma method, or a known coating method (such as a spin coating method, a dipping method, a casting method, an LB method, or an ink jet method) in which the organic compound is dissolved in an appropriate solvent.

When the layer is formed by a vacuum deposition method, a solution coating method, or the like, for example, crystallization is not likely to occur, and an excellent aging stability can be obtained. In addition, when film formation is performed by a coating method, a film may also be formed in combination with an appropriate binder resin.

As the above binder resin, although a poly(vinyl carbazole) resin, a polycarbonate resin, a polyester resin, an ABS resin, an acrylic resin, a polyimide resin, a phenol resin, an epoxy resin, a silicone resin, and an urea resin may be mentioned by way of example, the binder resin is not limited thereto.

In addition, these types of binder resins may be used alone as a homopolymer or a copolymer or may be used in combination. Furthermore, optionally, additives, such as a known plasticizer, antioxidant, and ultraviolet absorber, may also be used together.

(Application of Organic Light Emitting Element According to this Embodiment)

The organic light emitting element according to this embodiment may be used for a display device and a lighting device. In addition, the organic light emitting element according to this embodiment may also be used, for example, for an exposure light source of an image forming device of an electrophotographic system and a backlight of a liquid crystal display device.

The display device has the organic light emitting element according to this embodiment in a display portion. This display portion has a plurality of pixels. This pixel has the organic light emitting element according to this embodiment and an active element. As the active element, for example, a switching element or an amplifying element may be mentioned, and in particular, a transistor or an MIM element may be mentioned.

A drain electrode or a source electrode of the transistor is connected to the anode or the cathode of this organic light emitting element.

The display device may be used as an image display device of a personal computer (PC), a head mount display, a mobile phone, or the like. As an image to be displayed, any image, such as a two-dimensional image or a three-dimensional image, may be displayed.

The display device may be an image information processing device which has an image input portion to input image information from an area CCD, a linear CCD, a memory card, or the like, and which outputs an input image on the display portion.

The image information processing device may be a digital camera having an imaging optical system in which the image input portion is formed of an imaging element, such as a CCD sensor.

The display device may have an input function which can perform an input by touching an output image. For example, a touch-panel function may be mentioned.

In addition, the display device may also be used for a display portion of a multifunctional printer.

The organic light emitting element according to this embodiment may also be used for a lighting device. This lighting device has the organic light emitting element according to this embodiment and an AC/DC converter to supply a drive voltage thereto.

The color of light emitted from the lighting device according to this embodiment may be white, natural white, and any other colors.

In order to emit white light, the structure is formed in such a way that the light emitting portion of the organic light emitting element has a plurality of light emitting layers, the condensed polycyclic compound according to aspects of the present invention emits green light, and the other layers emit light other than the green light, so that the element emits white light.

The organic light emitting element according to this embodiment may be used for an exposure light source of an image forming device. The image forming device has a photo conductor, a charging portion to charge the photo conductor, an exposure portion to expose the photo conductor, and a developing unit to develop an electrostatic latent image. The organic light emitting element is used for the exposure portion.

The exposure light source has a plurality of light emitting points which are arranged to form at least one line. In addition, the light quantity of each of the light emitting points is independently controlled. These light emitting points are each formed of the organic light emitting element according to aspects of the present invention.

Figure 2:
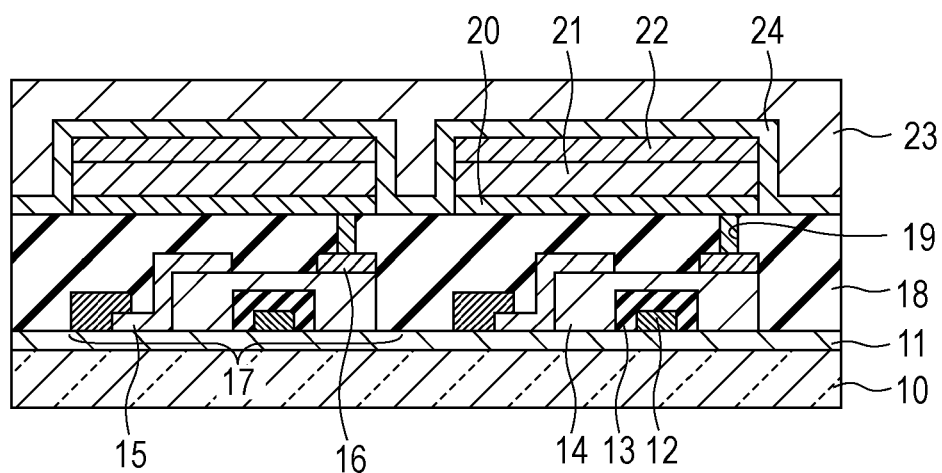
FIG. 2 is a schematic cross-sectional view showing the organic light emitting element according to the embodiment and a switching element connected thereto.

FIG. 2 is a schematic cross-sectional view of a display device having the organic light emitting element according to this embodiment and a TFT element, which is one example of the transistor, connected thereto.

This display device includes a substrate 10 formed of a glass or the like and a dampproof film 11 provided thereon to protect the TFT element or the organic compound layer. In addition, reference numeral 12 indicates a metal gate electrode. Reference numeral 13 indicates a gate insulating film, and reference numeral 14 indicates a semiconductor layer.

A TFT element 17 includes the semiconductor layer 14, a drain electrode 15, and a source electrode 16. An insulating film 18 is provided on an upper portion of the TFT element 17. An anode 20 of the organic light emitting element and the source electrode 16 are connected to each other through a contact hole 19.

The structure of the display device according to this embodiment is not limited to that described above and may have any structure as long as the anode or the cathode is connected to one of the source electrode and the drain electrode of the TFT element.

In this figure, although it is shown as if only one organic compound layer 21 is provided, a plurality of organic compound layers may also be provided. On a cathode 22, a first protective layer 23 and a second protective layer 24 are provided to suppress degradation of the organic light emitting element.

The emission luminance of the organic light emitting element according to this embodiment is controlled by a TFT element which is one example of the switching element. When a plurality of organic light emitting elements is provided in the plane, an image can be displayed by the emission luminance of each organic light emitting element.

The switching element of the organic light emitting element according to this embodiment is not limited to a TFT element, and a common transistor or an MIM element may also be used. In addition, the control may also be performed in such a way that active matrix drivers are formed on a Si substrate or the like, and the organic light emitting elements are provided thereon.

The structure may be selected depending on the degree of fineness, and for example, when the fineness is approximately QVGA, the structure in which the organic light emitting elements are provided on a Si substrate may be provided.

When a display device using the organic light emitting element according to this embodiment is driven, stable display with excellent image quality can be performed for a long time.

EXAMPLES

Example 1

Synthesis of Example Compound 104

(1) Synthesis of Intermediate BrCl-1

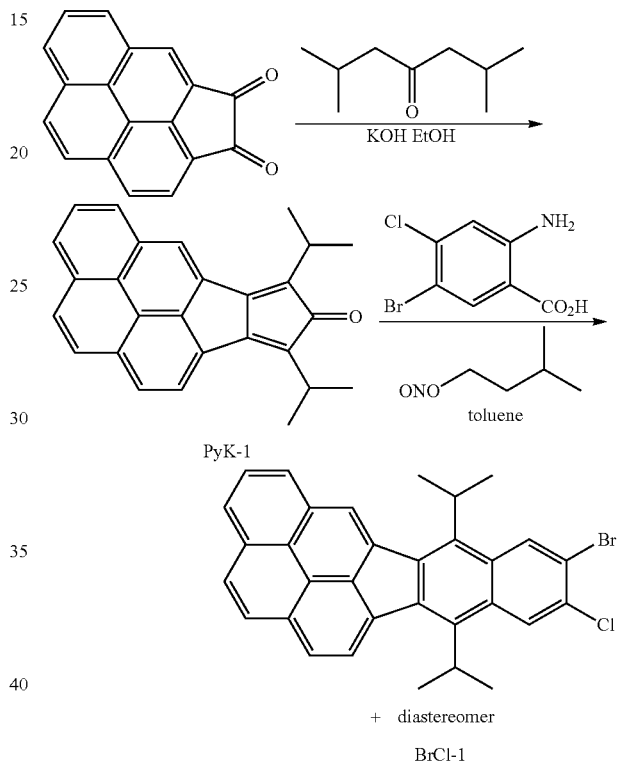

+ diastereomer

BrCl-1

The following reagents and solvent were charged in a 300-mL recovery flask.
Cyclopenta[cd]pyrene-3,4-dione: 4.00 g (15.6 mmol)
Diisobutyl ketone: 4.44 g (31.2 mmol)
Ethanol: 60 mL To this reaction solution, a solution prepared by dissolving 0.88 g (15.6 mmol) of potassium hydroxide in 15 mL of ethanol was slowly added dropwise at room temperature, and stirring was further performed for 10 hours.

After the reaction was completed, a mixture of water/methanol=1/1 was added to the reaction solution, and a precipitated product was filtrated and then dried, so that 1.97 g of the intermediate PyK-1 was obtained (yield: 35%).

Subsequently, the following reagents and solvent were charged in a 300-mL recovery flask.
Intermediate PyK-1: 1.97 g (5.43 mmol)
5-bromo-4-chloro anthranilic acid: 1.50 g (5.97 mmol)
Toluene: 100 mL Next, after this reaction solution was heated to 80° C., 0.79 mL (5.97 mmol) of isoamyl nitrite was added dropwise thereto, and the temperature was slowly increased to 110° C. Subsequently, heating and stirring were further performed for 2 hours.

After the reaction was completed, the reaction solution was washed with 1N hydrochloric acid and a saturated NaCl aqueous solution, was dried over sodium sulfate, was purified by column chromatography on silica gel (eluent: heptane/chloroform=4/1), and was further recrystallized from toluene to afford 1.93 g of the intermediate BrCl-1 in the form of a yellow powder (yield: 68%).

(2) Synthesis of Intermediate NpPh-1

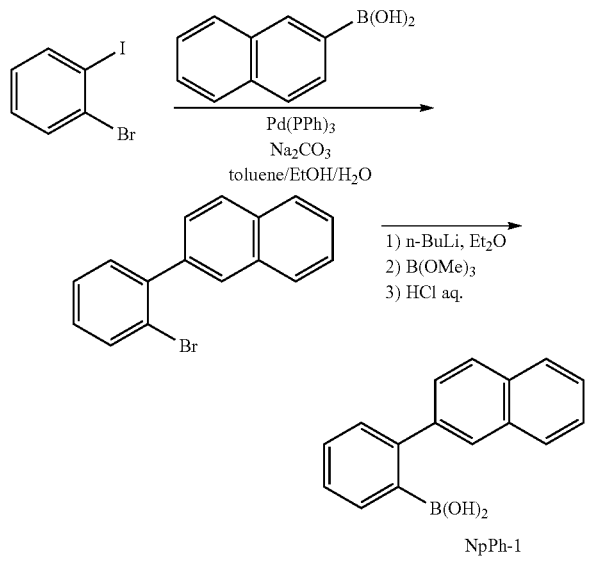

The following reagents and solvents were charged in a 200-mL recovery flask.

1-bromo-2-iodobenzene: 2.00 g (7.07 mmol)
2-naphthaleneboronic acid: 1.28 g (7.42 mmol)
Tetrakis(triphenylphosphine)palladium(0): 245 mg (0.212 mmol)
Toluene: 40 mL
Ethanol: 20 mL
10 wt % aqueous solution of sodium carbonate: 20 mL This reaction solution was heated and refluxed for 3.5 hours under nitrogen with stirring. After the reaction was completed, the reaction solution was washed with a saturated NaCl aqueous solution and was then dried over sodium sulfate followed by condensation, so that a crude product was obtained.

Furthermore, purification by column chromatography on silica gel (eluent: heptane/toluene=10/1) afforded 1.90 g of 2-(2-bromophenyl)naphthalene (yield: 95%).

Next, after 1.90 g (6.73 mmol) of 2-(2-bromophenyl)naphthalene was charged in a 200-mL three-necked flask equipped with a dropping funnel, and the inside of the flask was then replaced with nitrogen, 40 mL of diethyl ether was added, and this reaction solution was cooled to −78° C.

Subsequently, after 4.63 mL (7.40 mmol) of a hexane solution of n-butyl lithium at a concentration of 1.6 M was added dropwise to this reaction solution for 5 minutes, the temperature was slowly increased to 0° C. and was then again cooled to −78° C.

Next, after 1.00 mL (8.75 mmol) of trimethyl borate was added, the cooling was stopped, and the temperature was increased to room temperature. Furthermore, stirring was continued for 3 hours, and 70 mL of 2N hydrochloric acid was added, so that the reaction was quenched.

Subsequently, after a product was extracted with diethyl ether and was then washed with a saturated NaCl aqueous solution, dried over sodium sulfate followed by condensation, so that a crude product was obtained.

In addition, further purification was performed by short column chromatography on silica gel (eluent: chloroform/ethyl acetate=5/1) to afford 1.35 g of the intermediate NpPh-1 (yield: 81%).

(3) Synthesis of Example Compound 104

The following reagents and solvents were charged in a 50-mL recovery flask.

BrCl-1: 400 mg (0.764 mmol)
NpPh-1: 200 mg (0.802 mmol)
Tetrakis(triphenylphosphine)palladium(0): 26 mg (23 μmol)
Toluene: 12 mL
Ethanol: 6 mL
30 wt % aqueous solution of cesium carbonate: 6 mL This reaction solution was heated and refluxed for 3 hours under nitrogen with stirring. After the reaction was completed, a product was extracted with toluene and was then washed with a saturated NaCl aqueous solution, and dried over sodium sulfate followed by condensation, so that a crude product was obtained.

Furthermore, the crude was purified by column chromatography on silica gel (eluent: heptane/toluene=10/1) to afford 365 mg of the intermediate NpPhCl-1 (yield: 72%).

Subsequently, the following reagents were charged in a 50-mL recovery flask, and the inside thereof was replaced with nitrogen.

NpPhCl-1: 365 mg (0.550 mmol)

Palladium acetate: 7.4 mg (33 µmol)

Tricyclohexylphosphonium tetrafluoroborate: 24 mg (66 µmol)

Potassium carbonate: 152 mg (1.10 mmol)

Next, 5 mL of N,N-dimethylacetamide processed by nitrogen bubbling was added, and this reaction solution was heated at 130° C. for 5 hours under nitrogen with stirring.

After the reaction was completed, a product was extracted with toluene and was then washed with a saturated NaCl aqueous solution, and dried over sodium sulfate followed by condensation, so that a crude product was obtained.

Furthermore, after purified by column chromatography on silica gel (eluent: heptane/chloroform=5/1), recrystallization from toluene/heptane gave a crystal of the example compound 104.

After the crystal thus obtained was further processed by vacuum drying at 150° C., sublimation refining was performed at $10^{-4}$ Pa and 370° C., so that 130 mg of the example compound 104 having a high purity was obtained (yield: 39%).

Identification of the compound thus obtained was performed by mass analysis.

[MALDI-TOF-MS (Matrix-Assisted Laser Desorption-Ionization Time-of-Flight Mass Spectrometry)]

Measured value: m/z=610.48

Calculated value: $C_{48}H_{34}$=610.27

In addition, a fluorescence spectrum of a toluene diluted solution of the example compound 104 was measured at room temperature and an excitation wavelength of 350 nm. The wavelength of the maximum emission peak of the obtained fluorescence spectrum was 488 nm.

Example 2

Synthesis of Example Compound 205

(1) Synthesis of Intermediate BrCl-2

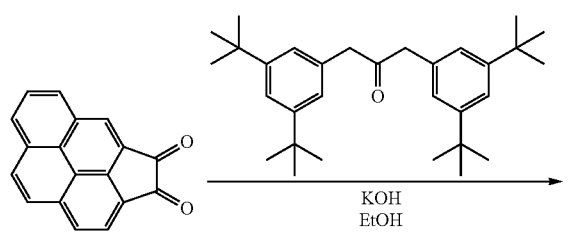

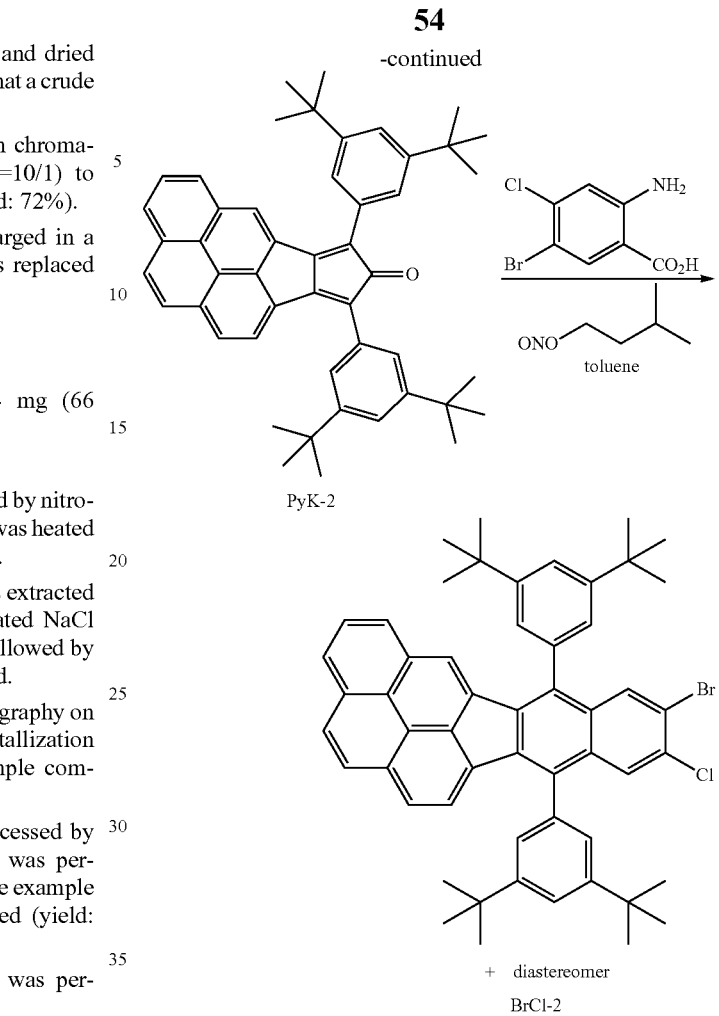

The following reagents and solvent were charged in a 200-mL recovery flask.

Cyclopenta[cd]pyrene-3,4-dione: 3.00 g (11.7 mmol)

1,3-bis(3,5-tert-butylphenyl)propane-2-one: 5.09 g (11.7 mmol)

Ethanol: 45 mL

After this reaction solution was heated to 70° C., a solution prepared by dissolving 0.66 g (11.7 mmol) of potassium hydroxide in 12 mL of ethanol was added to the reaction solution, and heating was further performed for 4 hours with stirring.

After the reaction was completed, a mixture of water/methanol=1/1 was added to the reaction solution, and a precipitated product was filtrated and then dried, so that 5.13 g of the intermediate PyK-2 was obtained (yield: 67%).

Subsequently, the following reagents and solvent were charged in a 300-mL recovery flask.

Intermediate PyK-2: 1.50 g (2.29 mmol)

5-bromo-4-chloro anthranilic acid: 631 mg (2.52 mmol)

Toluene: 75 mL

Next, after this reaction solution was heated to 80° C., 0.34 mL (2.52 mmol) of isoamyl nitrite was added dropwise thereto, and the temperature was slowly increased to 110° C. Subsequently, heating and stirring were further performed for 2 hours.

After the reaction was completed, the reaction solution was washed with 1N hydrochloric acid and a saturated NaCl aqueous solution, was dried over sodium sulfate, was then purified by column chromatography on silicagel (eluent: heptane/chloroform=4/1), and was further recrystallized from toluene to afford 1.40 g of the intermediate BrCl-2 in the form of a yellow powder (yield: 75%).

(2) Synthesis of Example Compound 205

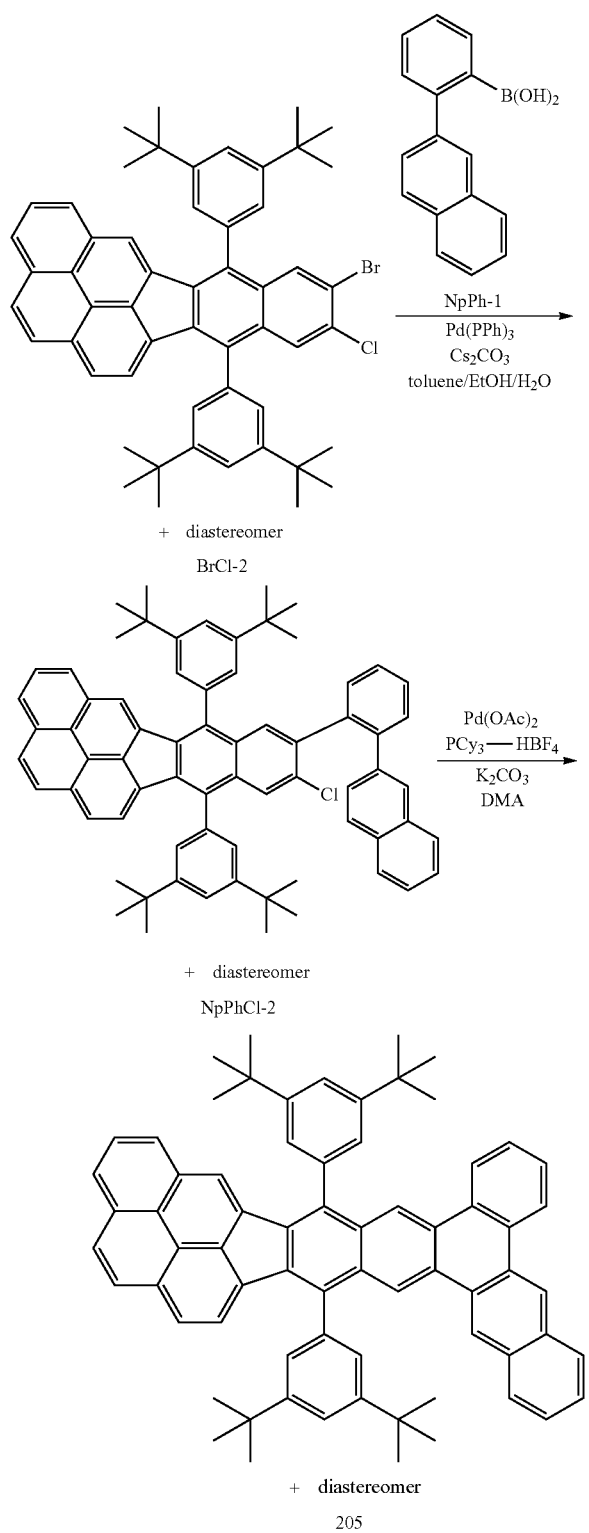

The following reagents and solvents were charged in a 100-mL recovery flask.
BrCl-2: 500 mg (0.612 mmol)
NpPh-1: 160 mg (0.643 mmol)
Tetrakis(triphenylphosphine)palladium(0): 21 mg (18 μmol)
Toluene: 16 mL
Ethanol: 8 mL
30 wt % aqueous solution of cesium carbonate: 8 mL This reaction solution was heated and refluxed for 4 hours under nitrogen with stirring. After the reaction was completed, a product was extracted with toluene and was then washed with a saturated NaCl aqueous solution, and dried over sodium sulfate followed by condensation, so that a crude product was obtained.

Furthermore, purification by column chromatography on silica gel (eluent: heptane/toluene=10/1), gave 407 mg of the intermediate NpPhCl-2 (yield: 71%).

Then, the following reagents were charged in a 50-mL recovery flask, and the inside thereof was replaced with nitrogen.
NpPhCl-2: 407 mg (0.433 mmol)
Palladium acetate: 6 mg (27 μmol)
Tricyclohexylphosphonium tetrafluoroborate: 20 mg (54 μmol)
Potassium carbonate: 120 mg (0.866 mmol)

Next, 5 mL of N,N-dimethylacetamide processed by nitrogen bubbling was added, and this reaction solution was heated at 130° C. for 10 hours under nitrogen with stirring.

After the reaction was completed, a product was extracted with toluene and was then washed with a saturated NaCl aqueous solution, and dried over sodium sulfate followed by condensation, so that a crude product was obtained.

Furthermore, after purified by column chromatography on silica gel (eluent: heptane/chloroform=5/1), recrystallization from toluene/heptane afforded a crystal of the example compound 205.

After the crystal thus obtained was further processed by vacuum drying at 150° C., sublimation refining was performed at $10^{-4}$ Pa and 390° C., so that 119 mg of the example compound 205 having a high purity was obtained (yield: 30%).

Identification of the compound thus obtained was performed by mass analysis.
[MALDI-TOF-MS]
Measured value: m/z=902.67
Calculated value: $C_{70}H_{62}$=902.49

In addition, a fluorescence spectrum of a toluene diluted solution of the example compound 205 was measured at room temperature and an excitation wavelength of 350 nm. The wavelength of the maximum emission peak of the obtained fluorescence spectrum was 490 nm.

Example 3

Synthesis of Example Compound 303

(1) Synthesis of Intermediate BrCl-3

(2) Synthesis of Intermediate NpPh-2

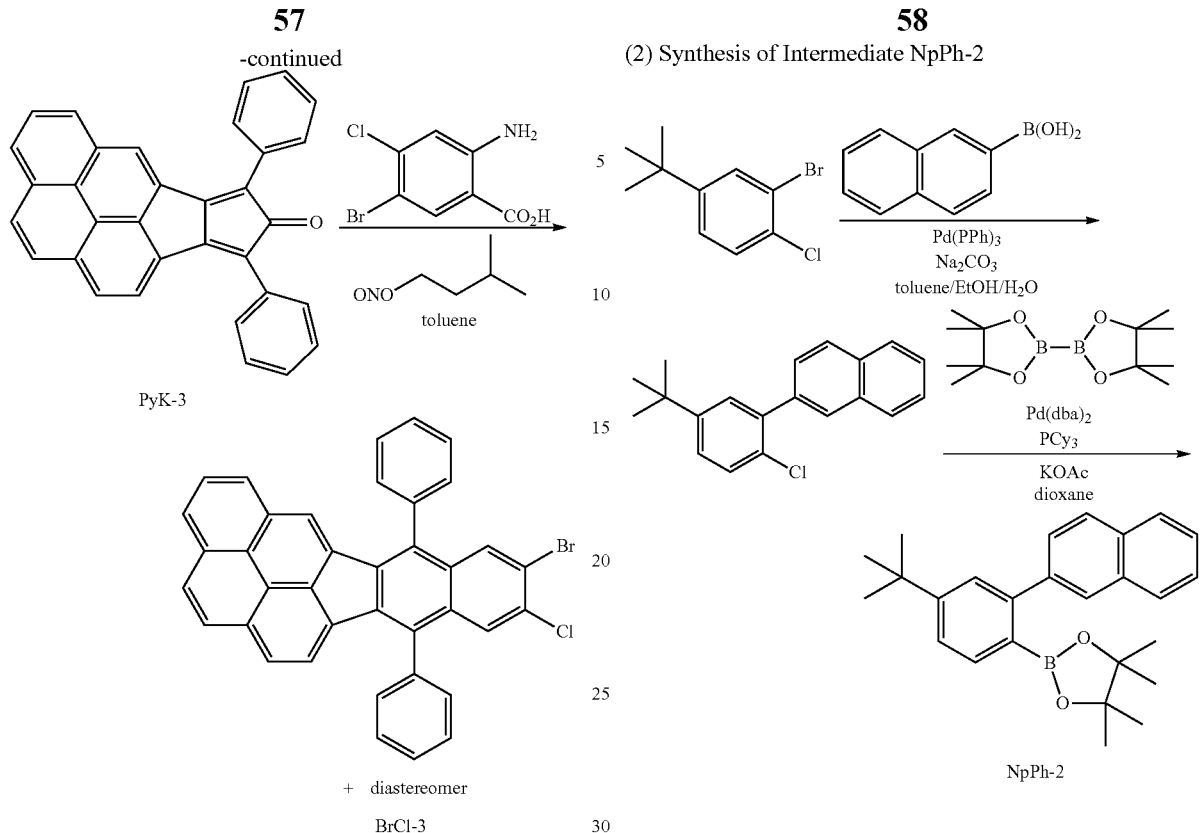

PyK-3

BrCl-3
+ diastereomer

NpPh-2

The following reagents and solvent were charged in a 200-mL recovery flask.
Cyclopenta[cd]pyrene-3,4-dione: 3.00 g (11.7 mmol)
1,3-diphenylpropane-2-one: 2.46 g (11.7 mmol)
Ethanol: 45 mL After this reaction solution was heated to 70° C., a solution prepared by dissolving 0.66 g (11.7 mmol) of potassium hydroxide in 12 mL of ethanol was added to the reaction solution, and heating was further performed for 3 hours with stirring.

After the reaction was completed, a mixture of water/methanol=1/1 was added to the reaction solution, and a precipitated product was filtrated and then dried, so that 3.68 g of the intermediate PyK-3 was obtained (yield: 73%).

Subsequently, the following reagents and solvent were charged in a 300-mL recovery flask.
Intermediate PyK-2: 2.00 g (4.65 mmol)
5-bromo-4-chloro anthranilic acid: 1.28 g (5.11 mmol)
Toluene: 100 mL Next, after this reaction solution was heated to 80° C., 0.68 mL (5.11 mmol) of isoamyl nitrite was added dropwise thereto, and the temperature was slowly increased to 110° C. Subsequently, heating and stirring were further performed for 3 hours.

After the reaction was completed, the reaction solution was washed with 1N hydrochloric acid and a saturated NaCl aqueous solution, was dried over sodium sulfate, and was then purified by 1 column chromatography on silica gel (eluent: heptane/chloroform=4/1).

Furthermore, recrystallization from toluene gave 2.04 g of the intermediate BrCl-3 in the form of a yellow powder (yield: 74%).

The following reagents and solvents were charged in a 200-mL recovery flask.
2-bromo-4-tert-butyl-1-chlorobenzene: 1.00 g (4.04 mmol)
2-naphthaleneboronic acid: 0.729 g (4.24 mmol)
Tetrakis(triphenylphosphine)palladium(0): 140 mg (0.121 mmol)
Toluene: 30 mL
Ethanol: 15 mL
10 wt % aqueous solution of sodium carbonate: 15 mL This reaction solution was heated and refluxed for 4 hours under nitrogen with stirring. After the reaction was completed, the reaction solution was washed with a saturated NaCl aqueous solution and was then dried over sodium sulfate followed by condensation, so that a crude product was obtained.

Furthermore, purification by column chromatography on silica gel (eluent: heptane/toluene=10/1) afforded 965 mg of 2-(2-tert-butyl-2-chlorophenyl)naphthalene (yield: 81%).

Then, the following reagents and solvent were charged in a 100-mL recovery flask.
2-(2-tert-butyl-2-chlorophenyl)naphthalene: 965 mg (3.27 mmol)
Bis(pinacolato)diboron: 996 mg (3.92 mmol)
Bis(dibenzylideneacetone)palladium(0): 94 mg (0.163 mmol)
Tricyclohexylphosphine: 138 mg (0.490 mmol)
Potassium acetate: 642 mg (6.54 mmol)
1,4-dioxane: 30 mL This reaction solution was stirred at 95° C. for 7 hours under nitrogen. After the reaction was completed, the reaction solution was washed with water and was then dried over sodium sulfate followed by condensation, so that a crude product was obtained.

Next, this crude product was purified by column chromatography on silica gel (eluent: heptane/toluene=1/1) to afford 733 mg of the intermediate NpPh-2 (yield: 58%).

(3) Synthesis of Example Compound 303

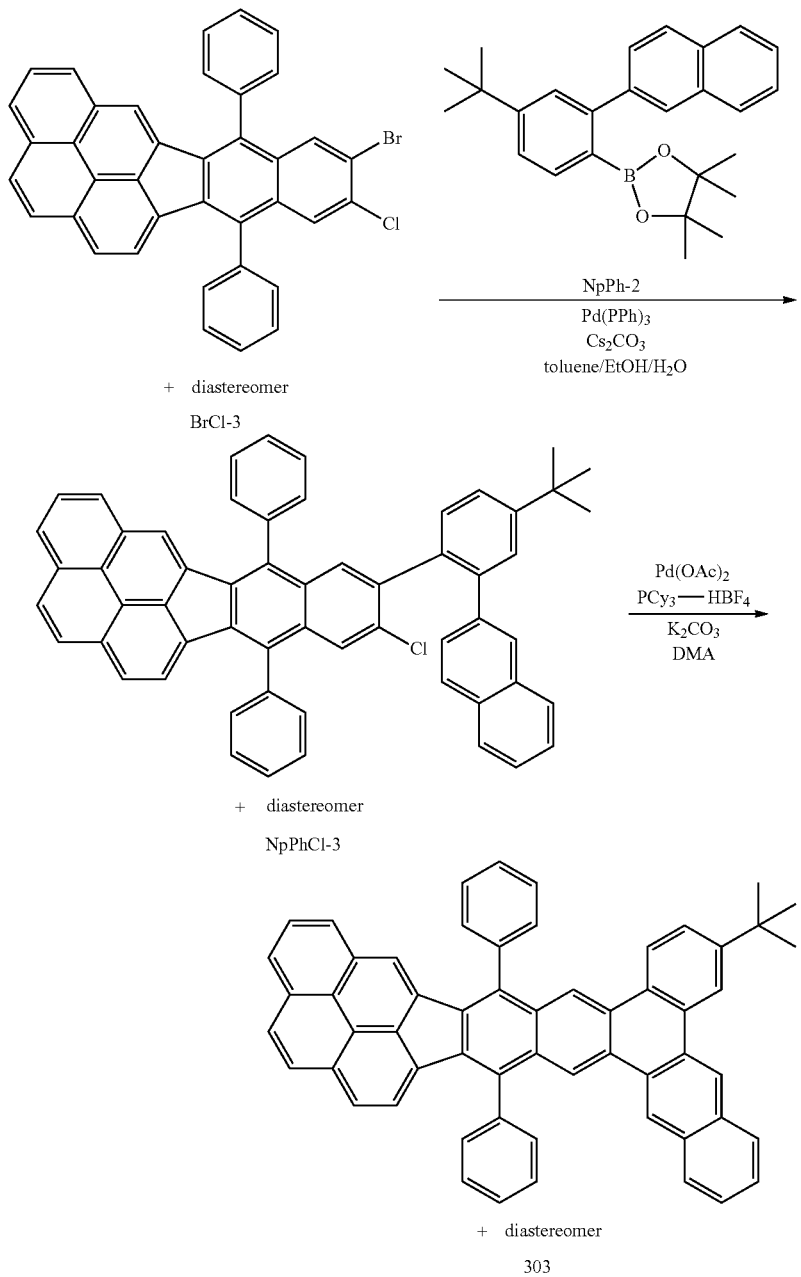

The following reagents and solvents were charged to a 100-mL recovery flask.
BrCl-3: 450 mg (0.760 mmol)
NpPh-2: 308 mg (0.798 mmol)
Tetrakis(triphenylphosphine)palladium(0): 26 mg (23 μmol)
Toluene: 14 mL
Ethanol: 7 mL
30 wt % aqueous solution of cesium carbonate: 7 mL This reaction solution was heated and refluxed for 3.5 hours under nitrogen with stirring. After the reaction was completed, a product was extracted with toluene and was then washed with a saturated NaCl aqueous solution, and dried over sodium sulfate followed by condensation, so that a crude product was obtained.

Furthermore, purification by column chromatography on silica gel (eluent: heptane/toluene=10/1) gave 497 mg of the intermediate NpPhCl-3 (yield: 83%).

Subsequently, the following reagents were charged in a 50-mL recovery flask, and the inside thereof was replaced with nitrogen.
NpPhCl-3: 497 mg (0.631 mmol)
Palladium acetate: 8.5 mg (38 μmol)
Tricyclohexylphosphonium tetrafluoroborate: 28 mg (76 μmol)
Potassium carbonate: 174 mg (1.26 mmol)

Next, 6 mL of N,N-dimethylacetamide processed by nitrogen bubbling was added, and this reaction solution was heated at 130° C. for 8 hours under nitrogen with stirring.

After the reaction was completed, a product was extracted with toluene and was then washed with a saturated NaCl aqueous solution, and dried over sodium sulfate followed by condensation, so that a crude product was obtained.

Furthermore, after purified by column chromatography on silica gel (eluent: heptane/chloroform=5/1), recrystallization from toluene/heptane afforded a crystal of the example compound 303.

After the crystal thus obtained was further processed by vacuum drying at 150° C., sublimation refining was performed at $10^{-4}$ Pa and 380° C., so that 190 mg of the example compound 303 having a high purity was obtained (yield: 41%).

Identification of the compound thus obtained was performed by mass analysis.
[MALDI-TOF-MS (Matrix-Assisted Laser Desorption-Ionization Time-of-Flight Mass Spectrometry)]
Measured value: m/z=734.46
Calculated value: $C_{58}H_{38}$=734.30

In addition, a fluorescence spectrum of a toluene diluted solution of the example compound 303 was measured at room temperature and an excitation wavelength of 350 nm. The wavelength of the maximum emission peak of the obtained fluorescence spectrum was 491 nm.

Example 4

Synthesis of Example Compound 401

(1) Synthesis of Intermediate NpPh-3

The following reagents and solvents were charged in a 200-mL recovery flask.
3-bromo-4-chloro-1',1'-biphenyl: 1.30 g (4.86 mmol)
2-naphthaleneboronic acid: 0.877 g (5.10 mmol)
Tetrakis(triphenylphosphine)palladium(0): 168 mg (0.146 mmol)
Toluene: 40 mL
Ethanol: 20 mL
10 wt % aqueous solution of sodium carbonate: 20 mL This reaction solution was heated and refluxed for 5 hours under nitrogen with stirring. After the reaction was completed, the reaction solution was washed with a saturated NaCl aqueous solution and was then dried over sodium sulfate followed by condensation, so that a crude product was obtained.

Furthermore, purification by column chromatography on silica gel (eluent: heptane/toluene=10/1) gave 1.22 g of 2-(4-chloro-[1',1'-biphenyl]-3-yl)naphthalene (yield: 80%).

Then, the following reagents and solvent were charged in a 100-mL recovery flask.
2-(4-chloro-[1',1'-biphenyl]-3-yl)naphthalene: 1.22 g (3.88 mmol)
Bis(pinacolato)diboron: 1.18 g (4.66 mmol)
Bis(dibenzylideneacetone)palladium(0): 112 mg (0.194 mmol)
Tricyclohexylphosphine: 163 mg (0.582 mmol)
Potassium acetate: 762 mg (7.76 mmol)
1,4-dioxane: 40 mL This reaction solution was stirred at 95° C. for 9 hours under nitrogen. After the reaction was completed, the reaction solution was washed with water and was then dried over sodium sulfate followed by condensation, so that a crude product was obtained.

Next, this crude product was purified by column chromatography on silica gel (eluent: heptane/toluene=1/1) to afford 946 mg of the intermediate NpPh-3 (yield: 60%).

(2) Synthesis of Example Compound 401

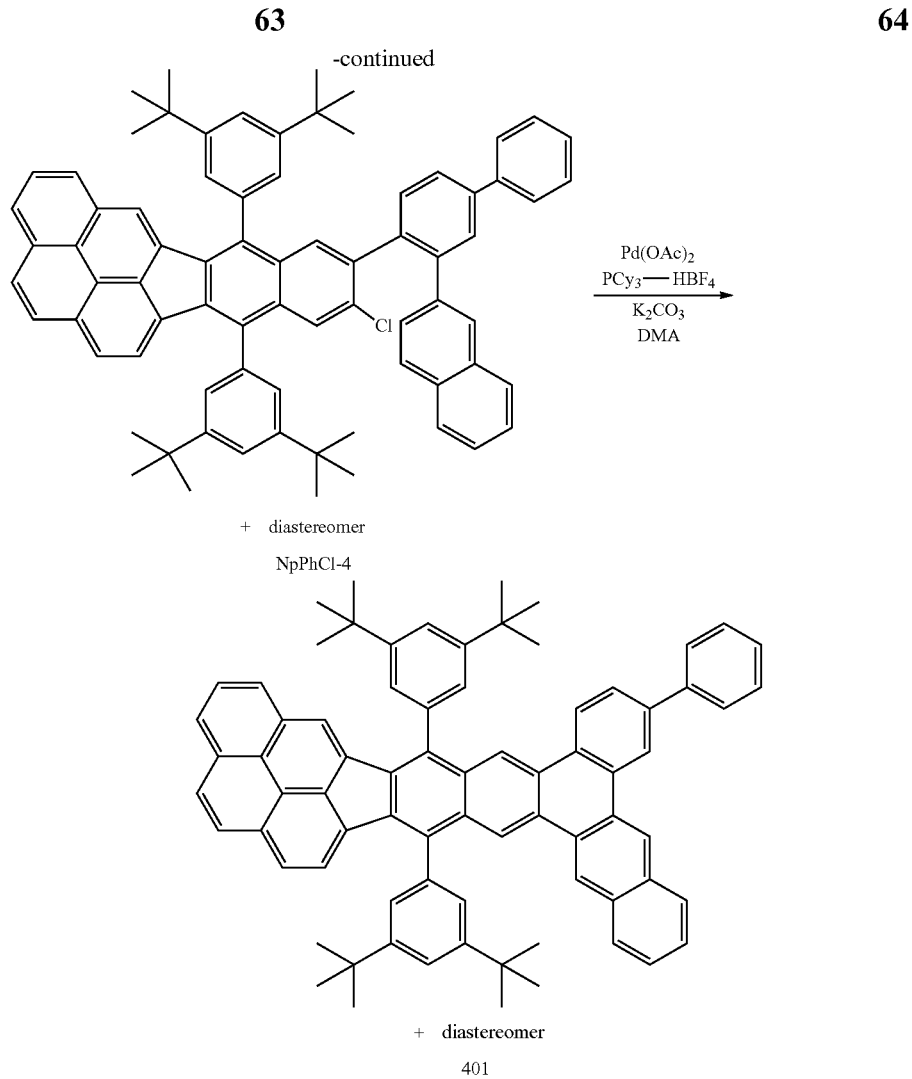

The following reagents and solvents were charged in a 100-mL recovery flask.
BrCl-2: 500 mg (0.612 mmol)
NpPh-3: 261 mg (0.643 mmol)
Tetrakis(triphenylphosphine)palladium(0): 21 mg (18 μmol)
Toluene: 16 mL
Ethanol: 8 mL
30 wt % aqueous solution of cesium carbonate: 8 mL This reaction solution was heated and refluxed for 4.5 hours under nitrogen with stirring. After the reaction was completed, a product was extracted with toluene and was then washed with a saturated NaCl aqueous solution, and dried over sodium sulfate followed by condensation, so that a crude product was obtained.

Furthermore, purification by column chromatography on silica gel (eluent: heptane/toluene=10/1) afforded 537 mg of the intermediate NpPhCl-4 (yield: 85%).

Then, the following reagents were charged in a 50-mL recovery flask, and the inside thereof was replaced with nitrogen.
NpPhCl-4: 537 mg (0.520 mmol)
Palladium acetate: 7 mg (31 μmol)
Tricyclohexylphosphonium tetrafluoroborate: 23 mg (62 μmol)
Potassium carbonate: 144 mg (1.04 mmol)

Next, 6 mL of N,N-dimethylacetamide processed by nitrogen bubbling was added, and this reaction solution was heated at 130° C. for 8.5 hours under nitrogen with stirring.

After the reaction was completed, a product was extracted with toluene and was washed with a saturated NaCl aqueous solution, and dried over sodium sulfate followed by condensation, so that a crude product was obtained.

Furthermore, after purified by column chromatography on silica gel (eluent: heptane/chloroform=5/1), recrystallization from toluene/heptane gave a crystal of the example compound 401.

After the crystal thus obtained was further processed by vacuum drying at 150° C., sublimation refining was performed at $10^{-4}$ Pa and 400° C., so that 178 mg of the example compound 401 having a high purity was obtained (yield: 35%).

Identification of the compound thus obtained was performed by mass analysis.
[MALDI-TOF-MS]
Measured value: m/z=978.72
Calculated value: $C_{76}H_{66}$=978.52

In addition, a fluorescence spectrum of a toluene diluted solution of the example compound 401 was measured at room temperature and an excitation wavelength of 350 nm. The wavelength of the maximum emission peak of the obtained fluorescence spectrum was 500 nm.

Comparative Example 1

Comparison of Maximum Emission Peak Wavelength

Fluorescence spectra of the following comparative compounds C1 and C2 were measured by a method similar to that of Example 1, and the wavelength of the maximum emission peak was measured. The results are shown in Table 2 together with the results of Examples 1 to 4.

C1

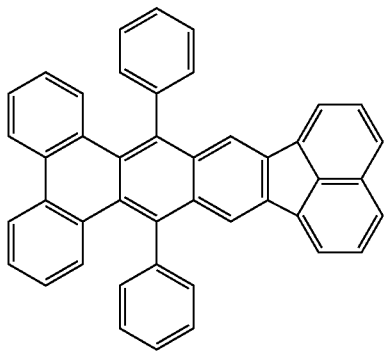

C2

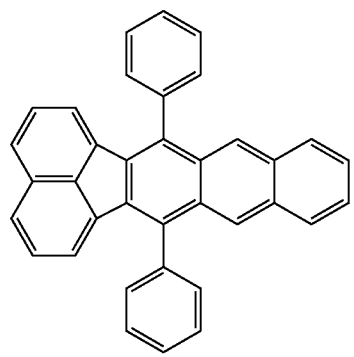

TABLE 2

| | Maximum Emission Peak Wavelength (In Toluene Diluted Solution) |
|---|---|
| Example Compound 104 | 488 nm |
| Example Compound 205 | 490 nm |
| Example Compound 303 | 491 nm |
| Example Compound 401 | 500 nm |
| Comparative Compound C1 | 460 nm |
| Comparative Compound C2 | 454 nm |

With respect to the green light emission having a maximum emission peak wavelength in a range of 475 to 510 nm, the example compounds according to aspects of the present invention satisfy the above condition and emit green light.

On the other hand, according to the comparative compound C1, a fluorantheno[8,9-b]triphenylene derivative, and the comparative compound C2, a naphtho[2,3-k]fluoranthene derivative, each of which has a main skeleton in which the number of condensed rings is smaller than that of the BTIPy main skeleton according to aspects of the present invention, the maximum emission peak wavelength is not in the range of the above green light emission, and blue light emission is exhibited.

Example 5

In this example, an organic light emitting element having the structure (6) in which an anode/hole transport layer/electron block layer/light emitting layer/hole block layer/electron transport layer/cathode were sequentially provided on a substrate in this order was formed by the following method.

An ITO film having a thickness of 120 nm formed as an anode on a glass substrate by a sputtering method was used as a transparent conductive support substrate (ITO substrate).

The following organic compound layers and electrode layers were successively formed on this ITO substrate using vacuum deposition performed by resistance heating in a vacuum chamber at a pressure of $10^{-5}$ Pa. In this case, the electrode surfaces facing each other were each formed to have an area of 3 mm$^2$.

Hole transport layer (40 nm) HT-1
Electron block layer (25 nm) EB-1
Light emitting layer (30 nm) Host material: H9, Guest material: Example compound 104 (1 wt %)
Hole block layer (10 nm) HB-1
Electron transport layer (30 nm) ET-1
Metal electrode layer 1 (0.5 nm) LiF
Metal electrode layer 2 (100 nm) Al

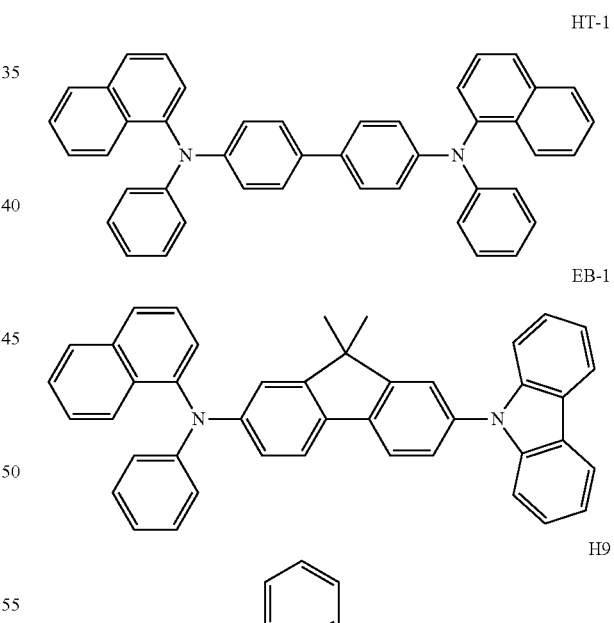

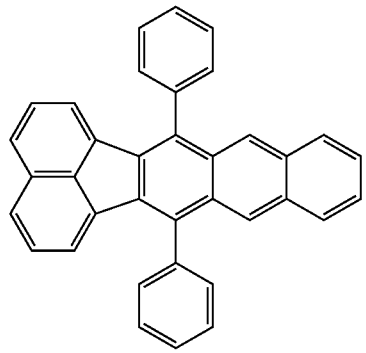

-continued

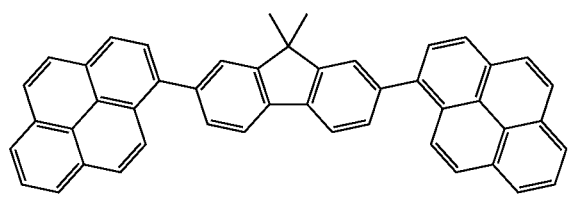
H11

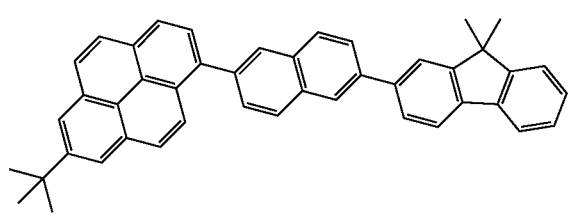
H14

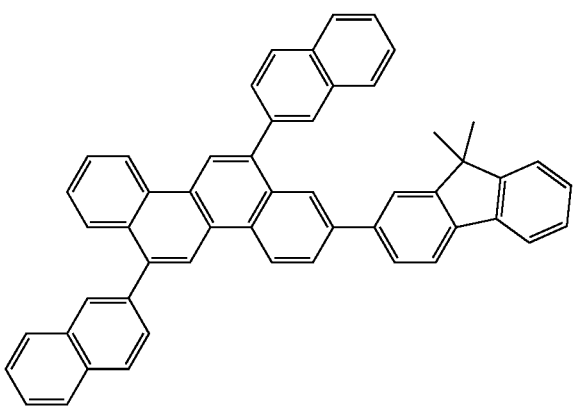
HB-1

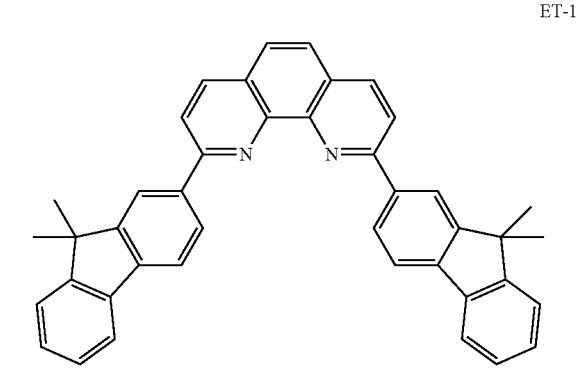
ET-1

Next, in order to prevent element degradation of the organic light emitting element caused by absorption of moisture, a protective glass plate was placed in a dry air atmosphere to cover the organic light emitting element and was sealed with an acrylic resin adhesive. The organic light emitting element was obtained as described above.

In the organic light emitting element thus obtained, when the ITO electrode was used as a positive electrode, the Al electrode was used as a negative electrode, and a voltage of 4.6 V was applied, green light emission having a light emitting efficiency of 17.1 cd/A and a luminance of 2,000 cd/m$^2$ was observed.

In addition, in this element, the CIE chromaticity coordinates were (x, y)=(0.27, 0.60), and the emission peak wavelength was 516 nm. Furthermore, in this light emitting device, a luminance half life at a constant current density of 100 mA/cm$^2$ was 541 hours.

Example 6

Except that the host material of the light emitting layer was changed from H9 to H11, and the guest material of the light emitting layer was changed from the example compound 104 to the example compound 205, an element was formed by a method similar to that of Example 5. In addition, the element thus obtained was evaluated in a manner similar to that of Example 5. The results are shown in Table 3.

Example 7

Except that the host material of the light emitting layer was changed from H9 to H14, and the guest material of the light emitting layer was changed from the example compound 104 to the example compound 303, an element was formed by a method similar to that of Example 5. In addition, the element thus obtained was evaluated in a manner similar to that of Example 5. The results are shown in Table 3.

Example 8

Except that the host material of the light emitting layer was changed from H9 to H11, and the guest material of the light emitting layer was changed from the example compound 104 to the example compound 401, an element was formed by a method similar to that of Example 5. In addition, the element thus obtained was evaluated in a manner similar to that of Example 5. The results are shown in Table 3.

Comparative Example 2

Except that the host material of the light emitting layer was changed from H9 to H14, and the guest material of the light emitting layer was changed from the example compound 104 to the comparative compound C2, an element was formed by a method similar to that of Example 5. In addition, the element thus obtained was evaluated in a manner similar to that of Example 5. The results are shown in Table 3.

TABLE 3

| | Guest Material of Light Emitting Layer | Host Material of Light Emitting Layer | @2000 cd/m$^2$ | | |
| | | | CIE Chromaticity | Applied Voltage (V) | Light Emitting Efficiency (cd/A) | Luminance Half Life @100 mA/cm$^2$ (hr) |
|---|---|---|---|---|---|---|
| Example 5 | Example Compound 104 | H9 | (0.27, 0.60) | 4.6 | 17.1 | 541 |
| Example 6 | Example Compound 205 | H11 | (0.28, 0.60) | 3.8 | 26.8 | 370 |

TABLE 3-continued

| Guest | Host | | @2000 cd/m² | | |
| | | | | | Luminance Half |
| Material of Light Emitting Layer | Material of Light Emitting Layer | CIE Chromaticity | Applied Voltage (V) | Light Emitting Efficiency (cd/A) | Life @100 mA/cm² (hr) |
|---|---|---|---|---|---|
| Example 7 | Example Compound 303 | H14 | (0.28, 0.61) | 4.0 | 25.0 | 349 |
| Example 8 | Example Compound 401 | H11 | (0.30, 0.62) | 3.7 | 27.3 | 320 |
| Comparative Example 2 | Comparative Compound C2 | H14 | (0.14, 0.22) | 4.7 | 5.7 | 177 |

Example 9

In this example, in an organic light emitting element having the structure (6) in which an anode/hole transport layer/electron block layer/light emitting layer/hole block layer/electron transport layer/cathode were sequentially provided on a substrate in this order, a laminated light emitting layer type white light emitting element was formed by the following method in which the light emitting layer was formed of three layers, a blue light emitting layer, a green light emitting layer, and a red light emitting layer.

The following organic compound layers and electrode layers were successively formed using vacuum deposition performed by resistance heating in a vacuum chamber at a pressure of $10^{-5}$ Pa on an ITO substrate formed by a method similar to that of Example 5. In this case, the electrode surfaces facing each other were each formed to have an area of 3 mm².

Hole transport layer (30 nm) HT-1
Electron block layer (10 nm) EB-1
Blue light emitting layer (10 nm) Host material: H14, Guest material: BD-1 (1 wt %)
Green light emitting layer (10 nm) Host material: H11, Guest material: Example compound 205 (1 wt %)
Red light emitting layer (7 nm) Host material: H11, Guest material: RD-1 (0.5 wt %)
Hole block layer (10 nm) HB-1
Electron transport layer (30 nm) ET-1
Metal electrode layer 1 (0.5 nm) LiF
Metal electrode layer 2 (100 nm) Al

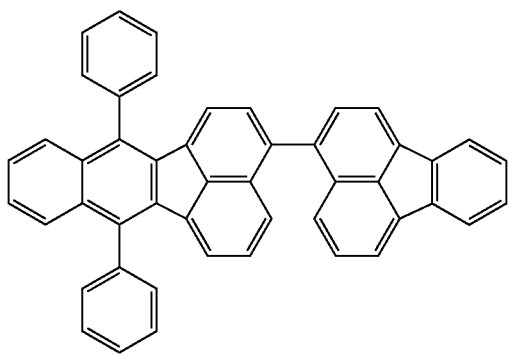

BD-1

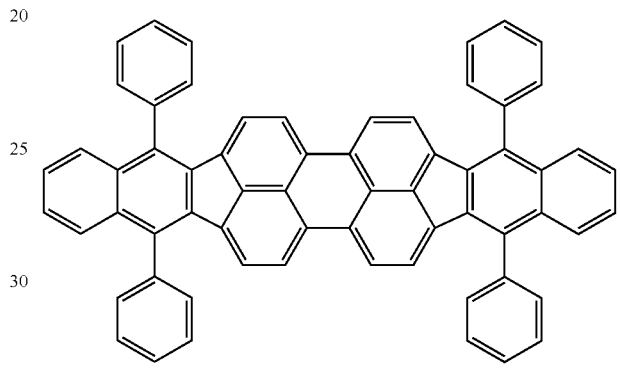

RD-1

Next, in order to prevent element degradation of the organic light emitting element caused by absorption of moisture, a protective glass plate was placed in a dry air atmosphere to cover the organic light emitting element and was sealed with an acrylic resin adhesive. The organic light emitting element was obtained as described above.

In the organic light emitting element thus obtained, when the ITO electrode was used as a positive electrode, the Al electrode was used as a negative electrode, and a voltage was applied, white light emission having CIE chromaticity coordinates (x, y) of (0.33, 0.36) was observed.

As has thus been described, the condensed polycyclic compound according to aspects of the present invention is a compound which emits green light and has a high chemical stability. Hence, an organic light emitting element which uses the condensed polycyclic compound according to aspects of the present invention for a guest material of its light emitting layer can exhibit green light emission having a high color purity, and a light emitting element having a high light emitting efficiency and a long life can also be provided. Furthermore, when the condensed polycyclic compound according to aspects of the present invention is used together with other light emitting materials which emit color light other than green light, a white light emitting element can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-181580 filed Aug. 23, 2011, which is hereby incorporated by reference herein in its entirety.

What is claimed is:

1. A condensed polycyclic compound represented by the following general formula [1] or [2]

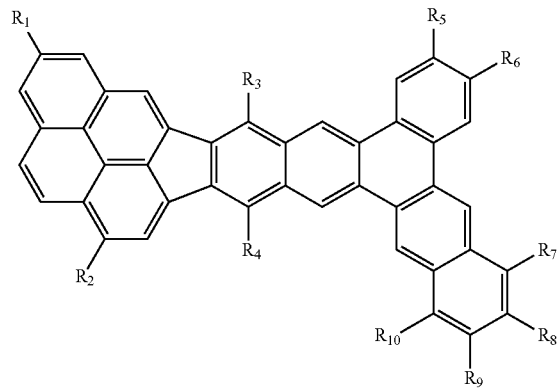

[1]

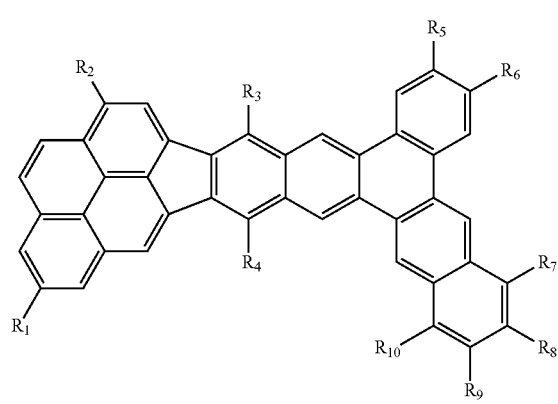

[2]

where in the formulas [1] and [2], $R_1$ to $R_{10}$ are each independently selected from the group consisting of a hydrogen atom, a straight or branched alkyl group having 1 to 4 carbon atoms, and a substituted or unsubstituted aromatic hydrocarbon group having 6 to 22 carbon atoms.

2. The condensed polycyclic compound according to claim 1, wherein the condensed polycyclic compound represented by the general formula [1] or [2] is a compound represented by the following general formula [3] or [4]

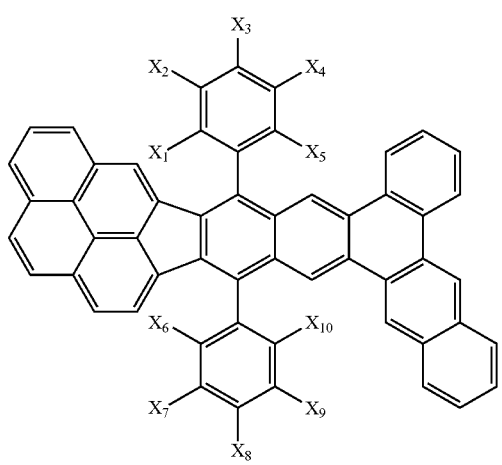

[3]

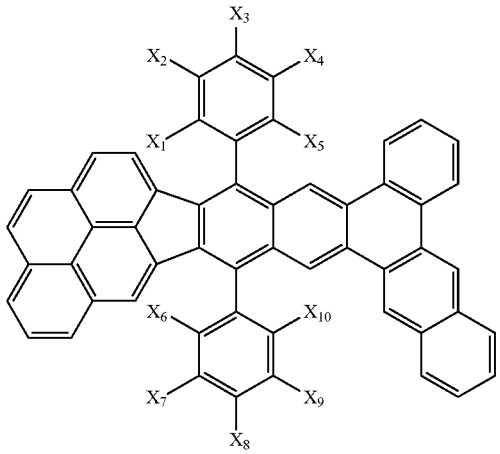

[4]

where in the formula [3] and [4], $X_1$ to $X_{10}$ are each independently selected from the group consisting of a hydrogen atom, a straight or branched alkyl group having 1 to 4 carbon atoms, and a substituted or unsubstituted phenyl group.

3. The condensed polycyclic compound according to claim 2, wherein the $X_2$, $X_4$, $X_7$, and $X_9$ each indicate the alkyl group.

4. The condensed polycyclic compound according to claim 1, wherein the condensed polycyclic compound exhibits green photoluminescence.

5. An organic light emitting element comprising:
a pair of electrodes; and
an organic compound layer arranged therebetween,
wherein the organic compound layer contains the condensed polycyclic compound according to claim 1.

6. The organic light emitting element according to claim 5, wherein the organic compound layer is a light emitting layer containing a host material and a guest material, and the guest material includes the condensed polycyclic compound.

7. The organic light emitting element according to claim 5, wherein the organic compound layer includes a plurality of light emitting layers,
at least one of the light emitting layers contains the condensed polycyclic compound, and
the light emitting layers emit different types of color light from each other so as to emit white light.

8. A display device comprising:
a plurality of pixels,
wherein at least one of the pixels includes the organic light emitting element according to claim 5 and an active element connected thereto.

9. An image information processing device comprising:
a display portion to display an image; and
an input portion to input image information,
wherein the display portion includes the display device according to claim 8.

10. A lighting device comprising:
the organic light emitting element according to claim 5; and
an AC/DC converter to supply a drive voltage thereto.

11. An image forming device comprising:
a photo conductor;
a charging portion to charge a surface of the photo conductor;
an exposure portion to expose the photo conductor; and
a developing unit to develop an electrostatic latent image formed on the photo conductor,
wherein the exposure portion includes the organic light emitting element according to claim 5.

12. An exposure light source to expose a photo conductor comprising:
a plurality of light emitting points,
wherein the light emitting points are arranged to form at least one line,
the light quantity of each of the light emitting points is independently controlled, and
the light emitting points each include the organic light emitting element according to claim 5.

* * * * *